United States Patent
Jin et al.

(10) Patent No.: US 8,968,699 B2
(45) Date of Patent: Mar. 3, 2015

(54) SWITCHABLE NANO-VEHICLE DELIVERY SYSTEMS, AND METHODS FOR MAKING AND USING THEM

(75) Inventors: Sungho Jin, San Diego, CA (US); Seunghan Oh, Jeonbuk (KR); Karla Brammer, La Jolla, CA (US); Seong Kong, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 369 days.

(21) Appl. No.: 12/741,590
(22) PCT Filed: Nov. 14, 2008
(86) PCT No.: PCT/US2008/083523
§ 371 (c)(1), (2), (4) Date: Aug. 9, 2010
(87) PCT Pub. No.: WO2009/064964
PCT Pub. Date: May 22, 2009

(65) Prior Publication Data
US 2010/0303716 A1    Dec. 2, 2010

Related U.S. Application Data

(60) Provisional application No. 60/988,387, filed on Nov. 15, 2007.

(51) Int. Cl.
| | |
|---|---|
| *A61K 51/00* | (2006.01) |
| *A61K 39/395* | (2006.01) |
| *A61K 39/00* | (2006.01) |
| *A61K 33/34* | (2006.01) |
| *A61K 33/24* | (2006.01) |
| *A61K 33/26* | (2006.01) |
| *A61K 33/28* | (2006.01) |
| *A61N 2/00* | (2006.01) |

(Continued)

(52) U.S. Cl.
CPC ............ *A61N 2/00* (2013.01); *A61M 37/0092* (2013.01); *A61N 7/00* (2013.01)
USPC ... 424/1.29; 424/1.11; 424/130.1; 424/133.1; 424/630; 424/635; 424/646; 424/647; 424/648; 424/649

(58) Field of Classification Search
None
See application file for complete search history.

(56) References Cited

U.S. PATENT DOCUMENTS

| 5,512,094 A | 4/1996 | Linton |
| 6,221,326 B1 | 4/2001 | Amiche |

(Continued)

FOREIGN PATENT DOCUMENTS

WO    WO 99/47253    9/1999

OTHER PUBLICATIONS

U.S. Patent Documents—None.*

(Continued)

*Primary Examiner* — Jeffrey T Palenik
(74) *Attorney, Agent, or Firm* — Gavrilovich, Dodd & Lindsey LLP

(57) ABSTRACT

The invention provides nanodevices or products of manufacture for use as drug delivery vehicles. In one aspect, the invention provides nanodevices or products of manufacture having on-off release mechanisms, e.g., that are "switchable", or "actuatable" (for example magnetically or ultrasonically switchable), for compounds contained within, e.g., for use as drug delivery nano-vehicles having on-off drug release mechanisms, and their therapeutic applications.

21 Claims, 21 Drawing Sheets

(51) Int. Cl.
*A61M 37/00* (2006.01)
*A61N 7/00* (2006.01)

(56) References Cited

U.S. PATENT DOCUMENTS

| | | | |
|---|---|---|---|
| 6,479,146 B1 | 11/2002 | Caruso et al. | |
| 6,720,007 B2 | 4/2004 | Walt et al. | |
| 2003/0082237 A1* | 5/2003 | Cha et al. | 424/490 |
| 2005/0058603 A1 | 3/2005 | Gao et al. | |
| 2007/0299518 A1* | 12/2007 | Ruane | 623/11.11 |
| 2008/0191828 A1* | 8/2008 | Gruner et al. | 335/284 |
| 2009/0220561 A1 | 9/2009 | Jin | |
| 2010/0303722 A1 | 12/2010 | Jin | |

OTHER PUBLICATIONS

Non-Patent Documents—None.*
Yugang Sun, et al. (2002) Template-Engaged Replacement Reaction: A One-Step Approach . . . Synthesis of Metal Nanostructures with Hollow Interiors, Nano Lett. 2(5):481-485.
S. W. Kim, et al. (2002) "Fabrication of Hollow Palladium Spheres and Their Successful Application . . . For Suzuki Coupling Reactions", J. Am. Chem. Soc. 124:7642-7643.
J. Y. Lee, et al. (2005) Uniform Coating of Nanometer-Scale BaTiO3 Layer . . . via Hydrothermal Conversion of Ti-Hydroxide, J. Am. Ceram. Soc. 88(2):303-307.
H. P. Liang, et al. (2005) Gold Hollow Nanospheres: Tunable Surface Plasmon Resonance Controlled by Interior-Cavity Sizes, J. Phys. Chem. B109, 7795-7800.
A. Jordan, et al. (2001) Pr . . . a new magnetic field therapy system for the treatment of human solid tumors with magnetic fluid hyperthermia, J. Magn. Magn. Mater. 225, 118-126.
V. S. Kalambur, et al. (2005) in vitro characterization of movement, heating and visualization of . . . nanoparticles for biomedical applications, Nanotechnology 16:1221-1233.
F. Scherer, et al. (2002) Magnetofection: enhancing and targeting gene delivery by magnetic force in vitro and in vivo, Nature/Gene Therapy 9(2):102-109.
Q. A. Pankhurst, et al. (2003) Applications of magnetic nanoparticles in biomedicine, J. Phys. D: Appl. Phys. 36, R167-R181.
C. Loo, et al (2005) Gold nanoshell bioconjugates for molecular imaging in living cells, Optics Lett. 30:1012-1014.
C. Loo, et al (2005) Immunotargeted Nanoshells for Integrated Cancer Imaging and Therapy, Nano Lett. 5(4):709-711.
Chen F., et al. (2005) Gold Nanocages: Bioconjugation and Their Potential Use as Optical Imaging Contrast Agents, Nano Lett. 5(3):473-477.
S. Jin, et al. (1987) Fe—Cr—Co Magnets (Invited), IEEE Trans. Magn. MAG-23:3187-3192.
S. Jin, et al. (1980) Low Cobalt Cr—Co—Fe Magnet Alloys by Slow Cooling Under Magnetic Field, IEEE Trans. Magnetics, MAG-16:526-528.
S. Jin, et al. (1984) Magnetic Sensors Using Fe—Cr—Ni Alloys with Square Hysteresis Loops, J. Appl. Phys. 55:2620-2622.
S. Jin, et al. (1999) Broad-Range Latchable Reconfiguration of Bragg Wavelength in Optical Gratings, Appl. Phys. Lett. 74:2259-2261.
R. Yoshida, et al. (1994) Modulating the Phase Transition Temperature and Thermosensitivity in N-isopropylacrilamide Copolymer Gels, J. Biomater. Sci., Polymer Ed. 6:585-588.
L. A. Guzman, et al. (1996) Local Intraluminal Infusion Biodegradable Polymeric Nanoparticles: . . . Prolonged Drug Delivery after Balloon Angioplasty Circulation 94(6):1441-1448.
Tai Hyun Kang, International Preliminary Report on Patentability and Written Opinion, May 29, 2009, KIPO as ISA for PCT.
Tai Hyun Kang, International Search Report, May 29, 2009, KIPO as ISA for PCT.

* cited by examiner

SWITCHABLE NANO-VEHICLE DELIVERY SYSTEMS, AND METHODS FOR MAKING AND USING THEM

CROSS-REFERENCE TO RELATED APPLICATIONS

This United States utility patent application is the §371 national phase of PCT international patent application no. PCT/US2008/083523 having an international filing date of Nov. 14, 2008, which claims benefit of priority to U.S. Provisional Patent Application Ser. No. 60/988,387, filed Nov. 15, 2007. The aforementioned applications are expressly incorporated herein by reference in their entirety and for all purposes.

FIELD OF THE INVENTION

The invention provides nanodevices or products of manufacture for use as drug delivery vehicles. In one aspect, the invention provides nanodevices or products of manufacture having on-off release mechanisms, e.g., that are "switchable", or "actuatable" (for example magnetically or ultrasonically switchable), for compounds contained within, e.g., for use as drug delivery nano-vehicles having on-off drug release mechanisms, and their therapeutic applications.

BACKGROUND

Hollow spheres have received much attention in recent years for a variety of technical applications including potential controlled-rate, drug release vehicles; see references 12 to 16 (as cited below).

Some of the hollow nanospheres (~50-200 nm diameter) have pores on the shell as evidenced by the chemical dissolution of interior materials for hollow particle synthesis. This can allow a passive drug delivery based on slowed-down kinetics. However, there is no convenient, known way of triggered drug release from such nanospheres.

There are many drug delivery mechanisms investigated by previous researchers based on temperature-responsive polymers and hydrogels such as poly(NIPPAm), see references 1 to 5, listed below. However, most of these studies deal with slow release from such polymers or one time temperature change on implanting to human body.

SUMMARY

The invention provides nanodevices or products of manufacture for use as drug delivery vehicles. In one aspect, the invention provides nanodevices or products of manufacture having on-off release mechanisms, e.g., that are "switchable", or "actuatable", for compounds contained inside them, e.g., for use as drug delivery nano-vehicles having on-off drug or biological agent release mechanisms, and their therapeutic applications. The invention provides nanodevices or products of manufacture and methods for controlled drug release therapeutics and for research; and in one aspect the invention provides an on-off switchable (actuatable) drug delivery vehicle. In one embodiment, the invention provides nanodevices or products of manufacture that are nanotechnology-based, magnetically or ultrasonically switchable (actuatable), e.g., as drug delivery vehicles. In one embodiment, the nanodevices or products of manufacture have remotely on-off switchable release capability.

The invention provides alternative embodiments of the magnetically or ultrasonically actuatable (switchable) nanodevices or products of manufacture (e.g., as drug-delivery biomaterials) of the invention: hollow multifunctional nanospheres with magnetically or ultrasonically triggerable drug release; nano-reservoir array with magnetically latchable valves; and/or re-entrant nano-depot arrays with remotely triggerable, temperature-sensitive valves.

Biological agents that can be stored in (and delivered by) the nanostructure devices and products of manufacture of this invention include growth factors, collagens, various proteins/biomolecules, genes, enzymes, hormones, DNAs, antibiotics, drugs, and functional nanoparticles. The nanodevices or products of manufacture of the invention can comprise any desired material, composition or agent, e.g., drugs, growth factors, hormones, proteins, enzymes, antibiotics, antibodies, DNA, nanoparticles, vitamins and minerals, air fresheners, gas-generating compounds (such as for oxygen, nitrogen, air, ozone or chlorine), or any chemicals.

The nanostructured substrates can be manufactured to allow one or more of various reagents, drugs, chemicals, gases or biological agents to be controllably released, e.g., for drug treatments, for prophylactic reasons, for enhancing or inhibiting cell growth, e.g., stem cell growth or cancer stem cell inhibition, for guided differentiation into specific type of cells, such as cancer cells, for enhancing hepatocyte growth, for treating cancer tumors, for therapeutic insulin delivery, for stimulating vascularization and/or other cell growth and functionalities.

The nanodevices or products of manufacture of the invention can be administered in any manner, e.g., as inserted floating particles in the blood stream, in any body fluid or cavity, inside or near any tissue or organ, as subcutaneous or intradermal implants or in transplantations, including in implants comprising a three-dimensional array.

The nanodevices or products of manufacture of the invention can be administered with any cell type, e.g., compounds contained in nanodevices or products of manufacture of the invention can be for accelerating bone growth for orthopedic and dental repair; in vivo and in vitro accelerated growth of cells including functional cells (such as liver cells, kidney cells, nerve cells, myocytes, stem cells) or supportive tissues (soft tissues such as muscles, tendons, fibrous tissues, periodontal tissues, fat, blood vessels, or hard tissues such as bone and teeth), proliferation and/or harvesting of cells to be supplied for therapeutics and laboratory experiments, particularly rare cell types such as stem cells or disease cells; therapeutic applications for local sustained drug release; and rapid diagnosis of cell-based conditions, toxicities and/or diseases involved in, for example, infections, epidemics and/or biological warfare agent or toxin exposures.

The invention provides products of manufacture or nanodevices that are magnetically, thermally or ultrasonically actuatable to release a compound or a cell stored within, comprising:

(a) (i) a plurality of hollow nanospheres comprising a magnetically, thermally or ultrasonically triggerable (magnetic, thermal or ultrasonic responsive) compound release capability, wherein the nanodevice when triggered by remote activation release the compound or cell stored within the nanospheres;

(ii) a nano-reservoir array with a plurality of magnetically latchable valves, wherein the valves when triggered release the compound or cell stored within the nanospheres of (i), the nano-reservoirs of (ii); and/or (iii) a re-entrant nano-depot array with a plurality of remotely triggerable, temperature-sensitive valves, wherein the valves when triggered release the compound or cell stored in the re-entrant nano-depot array; or (b) the product of manufacture or a nanodevice of (a), wherein the nanospheres or the valves are triggered by remote activation.

In alternative embodiments, the products of manufacture or nanodevices comprise (a) gold (Au), platinum (Pt), palladium (Pd), silica, silicon dioxide ($SiO_2$) or a polymer, or a graphite shell, or Ni, Cu, Co and/or Fe particles, or Ni, Cu, Co and/or Fe oxide particles;

(b) a coating, layer or shell comprising a metal layer;

(c) a coating, layer or shell comprising a Au, a Pt, a Pd, a stainless steel or an alloy thereof, or Ni, Cu, Co and/or Fe oxide particles;

(d) a coating, layer or shell comprising a ceramic, a silicon oxide, an aluminum oxide, a titanium oxide, a carbon or a carbide, a graphite, a Ti-carbide, a Zr-carbide, a Si-carbide, or a polymer;

(e) the product of manufacture or nanodevice of (b), wherein the polymer comprises a polystyrene or a polymethyl methacrylate (PMMA);

(f) the coating, layer or shell of (e) as deposited on the product of manufacture or nanodevice by chemical precipitation, sol-gel synthesis, emulsion processing, displacement reactions, electroless deposition, electrochemical deposition, or chemical or physical vapor deposition inside a fluidized bed;

(g) trapped nanoparticles within the hollow nanospheres or nano-reservoirs, wherein the nanoparticles comprise a metal, ceramic or polymer with an average diameter of between about 5 to 200 nm, or between about 10 to 100 nm, or between about 20 to 80 nm, or about 1, 2, 3, 4, 5, 6, 7, 8, 9 or 10 nm;

(h) the product of manufacture or nanodevice of (g), wherein the trapped nanoparticles comprise: (1) oxides of Fe, Ni, Co, or their alloys, or (2) alloys comprising at least one of an element of (1), and further comprising other elements of less than 50 atomic %; or (i) the product of manufacture or nanodevice of (g), wherein the nanoparticles comprise, or further comprise, a partially oxidized surface to protect against further oxidation, or the nanoparticles comprise, or further comprise, an inert metal coated surface.

In alternative embodiments of the products of manufacture or nanodevices of the invention:

(i) the product or device is magnetically actuatable by:
(a) comprising (containing within) a ferromagnetic nanoparticle, a superparamagnetic nanoparticle, biocompatible $Fe_3O_4$ (magnetite) or $Fe_2O_3$ (maghemite) particles, a particle comprising $Fe_2O_3$ or $Fe_3O_4$, or a "chain-of-sphere" nanomagnet particles;
(b) by comprising (containing within) at least 10, or at least 100, or at least 1000 particles of (a); or
(c) comprising (containing within) the particles of (a) or (b) that are between about 5 to 200 or more, or between about 10 to 100 or more, or about 1, 2, 3, 4, 5, 10, 15, 20, 25, 30, 35, 40, 45, 50, 55, 60, 65, 70, 75, 80, 85, 90, 95 or 100 or more nm in diameter; or (ii) the product or device is ultrasonically or thermally actuatable by
(a) comprising (containing within) a nonmagnetic nanoparticle, ferromagnetic nanoparticle, a superparamagnetic nanoparticle, a biocompatible $Fe_3O_4$ (magnetite) or $Fe_2O_3$ (maghemite) particle, a particle comprising $Fe_2O_3$ or $Fe_3O_4$, or a "chain-of-sphere" nanomagnet particles;
(b) by comprising (containing within) at least 10, or at least 100, or at least 1000 particles of (a); or
(c) comprising (containing within) the particles of (a) or (b) that are between about 5 to 200 or more, or between about 10 to 100 or more, or about 1, 2, 3, 4, 5, 10, 15, 20, 25, 30, 35, 40, 45, 50, 55, 60, 65, 70, 75, 80, 85, 90, 95 or 100 or more nm in diameter.

In alternative embodiments, the products of manufacture or nanodevices of the invention comprise a compound that can be or comprises (e.g., can have contained therein) a drug or pharmaceutical composition, a biological agent, a protein, a chemical, a gas-generating compound, a drug, a tracer or marker, or an inorganic nanoparticle, or the cell comprises a mammalian or a human cell, or a bacterial or a yeast cell. In alternative embodiments, the tracer or marker comprises a quantum dot or a fluorescent dye, a luminescent image tracer or marker, a nuclear medicine imaging tracer or marker, a positron emission tomography (PET) imaging compound, a 18-fluorodeoxyglucose, e.g., a [18F]-2-fluoro-2-deoxyglucose, 6-[$^{18}$F]-fluoro-L-dopa (FDOPA), or a [18F]-3'-fluoro-3'-deoxythymidine. In alternative embodiments, the compound or drug comprises a biologic, an antibiotic, an antiviral agent, an antibody, a humanized therapeutic antibody, an insulin, a cytokine or a hormonal protein, a steroid, an antibiotics medicine, a dexamethasone, an anti-inflammatory or an immunosuppressant steroid, a cancer therapy compound, a paclitaxel (TAXOL™), a mitotic inhibitor drug used in cancer chemotherapy, a 1,3-bis(2-chloroethyl)-1-nitrosourea (BCNU), a radioactive isotope, a polysaccharide, a nucleic acid or a vector or plasmid.

In alternative embodiments, the product of manufacture or nanodevice comprises (a) a biodegradable and/or bioabsorbable material or shell; or (b) a biodegradable and/or bioabsorbable material or shell comprising a poly lactic acid (PLA) polymer, a glycollic acid polymer, a polylactic-polyglycolic acid (PLGA) copolymer, a dextran, a dextran grafted with a poly (N-isopropylacrylamide-co-N,N-dimethylacrylamide) or an elastomeric poly (phosphoester urethane), a polycaprolactone (PCL) polymer, a polyhydroxybutyrate (PHB) polymer, a PEG modified PLGA or a surface modified PLGA with poly(L-lysine)-g-poly(ethylene glycol) (PLLg-PEG).

The invention provides hollow nanospheres comprising (having contained within) one or a plurality of magnetic particles and a compound or a cell. In alternative embodiments, the nanospheres of the invention comprise (or further comprise):

(a) gold (Au), platinum (Pt), palladium (Pd), silica, silicon dioxide ($SiO_2$), polymer, or graphite shells, and Ni, Cu, Co and/or Fe particles or oxide particles of Ni, Cu, Co and/or Fe;

(b) a coating, layer or shell comprising:
(i) a ceramic based layer, or a ceramic based layer comprising a compound selected from the group consisting of a silicon oxide, an aluminum oxide, a titanium oxide, a carbon or a carbide, a graphite, a Ti-carbide, a Zr-carbide and a Si-carbide,
(ii) a silicon oxide, an aluminum oxide, a titanium oxide, a carbon or a carbide, a graphite, a Ti-carbide, a Zr-carbide and a Si-carbide,
(iii) a polymer based layer, or a polymer based layer selected from the group consisting of a polystyrene and a polymethyl methacrylate (PMMA), or
(iv) a metal layer, or a metal layer selected the group consisting of a Au, a Pt, a Pd, a stainless steel or an alloy thereof, and oxide particles of Ni, Cu, Co and/or Fe;

(c) the coating, layer or shell of (b), as deposited on the product of manufacture or nanodevice by chemical precipitation, sol-gel synthesis, emulsion processing, displacement reactions, electroless deposition, electrochemical deposition, or chemical or physical vapor deposition inside a fluidized bed;

(d) trapped nanoparticles within the nanosphere, wherein the nanoparticles comprise a metal, ceramic or polymer having an average diameter of between about 5 to 200 or more, or between about 10 to 100 or more, or about 1, 2, 3, 4, 5, 10, 15, 20, 25, 30, 35, 40, 45, 50, 55, 60, 65, 70, 75, 80, 85, 90, 95 or 100 or more nm in diameter;

(e) nanoparticles within the nanosphere comprising: (1) oxides of Fe, Ni, Co, or their alloys, or (2) the nanoparticle of (1) comprising, or further comprising, at least one of element of (1) and other elements of less than 50 atomic %; or (f) nanoparticles comprising metals or alloys with a partially oxidized surface to protect against further oxidation, or nanoparticles of metals or alloys having inert metal coated surface.

In alternative embodiments, the coating or shell is deposited on the nanosphere by chemical precipitation, sol-gel synthesis, emulsion processing, displacement reactions, electroless deposition, electrochemical deposition, or chemical or physical vapor deposition inside a fluidized bed. In alternative embodiments, the one or the plurality of magnetic particles comprises (has contained within): (a) a ferromagnetic nanoparticle, a superparamagnetic nanoparticle, biocompatible $Fe_3O_4$ (magnetite) or $Fe_2O_3$ (maghemite) particles, a particle comprising $Fe_2O_3$ or $Fe_3O_4$, or a "chain-of-sphere" nanomagnet particle; (b) at least 10, or at least 100, or at least 1000 particles of (a); or (c) the particles of (a) or (b) that are between about 10 to 30 nm, or 5 to 50 nm in diameter.

In alternative embodiments, the product of manufacture, nanodevice and/or nanosphere further comprises a targeting molecule or a molecule that enhances receptor-mediated endocytosis on its surface. In alternative embodiments, the targeting molecule on the nanosphere surface comprises an antibody, an antiviral agent, a ligand for a cell surface receptor, a cytokine, a transferrin, an albumin, a knock-out serum albumin (KSA), or a polysaccharide.

In alternative embodiments, the product of manufacture, nanodevice and/or nanosphere of the invention comprises (a) a biodegradable and/or bioabsorbable material or shell; or (b) a biodegradable and/or bioabsorbable material or shell comprising a poly lactic acid (PLA) polymer, a glycollic acid polymer, a polylactic-polyglycolic acid (PLGA) copolymer, a dextran, a dextran grafted with a poly (N-isopropylacrylamide-co-N,N-dimethylacrylamide) or an elastomeric poly (phosphoester urethane), a polycaprolactone (PCL) polymer, a polyhydroxybutyrate (PHB) polymer, a PEG modified PLGA or a surface modified PLGA with poly(L-lysine) -g-poly(ethylene glycol) (PLLg-PEG).

In alternative embodiments, the product of manufacture, nanodevice and/or nanosphere of the invention comprises a drug, a biological agent, a polypeptide, a polysaccharide, a nucleic acid, a chemical, a drug, a tracer or an inorganic nanoparticle, or the cell comprises a mammalian or a human cell, or a bacterial or a yeast cell. The biological agent, nucleic acid or polypeptide can comprise an antibiotic, an antibody, an antiviral agent, an enzyme, a transcript, a gene, an RNA molecule, a DNA molecule, a biomolecule, a cytokine, a hormone or a growth factor. The tracer or marker can comprise a quantum dot or a fluorescent dye, a luminescent image tracer or marker, a nuclear medicine imaging tracer or marker, a positron emission tomography (PET) imaging compound, a 18-fluorodeoxyglucose, e.g., a [18F]-2-fluoro-2-deoxyglucose, 6-[$^{18}$F]-fluoro-L-dopa (FDOPA), or a [18F]-3'-fluoro-3'-deoxythymidine. The compound or drug can comprise a biologic, an antibiotic, an antiviral agent, an antibody, a humanized therapeutic antibody, an insulin, a cytokine or a hormonal protein, a steroid, a dexamethasone, an anti-inflammatory or an immunosuppressant steroid, a cancer therapy compound, a paclitaxel (TAXOL™), a mitotic inhibitor drug used in cancer chemotherapy, a 1,3-bis(2-chloroethyl)-1-nitrosourea (BCNU), a radioactive isotope, a polysaccharide, a nucleic acid or a vector or plasmid.

In alternative embodiments, the product of manufacture, nanodevice and/or nanosphere of the invention comprises further comprises (or has designed on its surface) (a) a plurality of pores or nanopores on the nanosphere surface; (b) a plurality of nanopores on the nanosphere surface made by partial sintering shrinkage in a nanosphere shell material; (c) a plurality of nanopores on the nanosphere surface made by chemical or acid etching; (d) a plurality of nanopores on the nanosphere surface made by partial burning of a nanosphere coating polymer using high temperature annealing; or (e) a plurality of nanopores on the nanosphere surface having an average pore size in the semi-hollow or hollow sphere shell the range of between about 1 to 40 nm, or 2 to 20 nm, or 5 to 10 nm, in diameter.

In alternative embodiments, the product of manufacture, nanodevice and/or nanosphere of the invention comprises (a) a surface or a surface coating comprising an etchable metal or polymer composition, and a plurality of nanopores is created on the surface by chemical or acid etching of the etchable metal or polymer composition; or (b) the nanosphere of (a), wherein the etchable metal comprises an iron oxide, a copper (Cu), a nickel (Ni) or an alloy thereof, or the polymer comprises a polystyrene or a polymethyl methacrylate (PMMA). The nanospheres can comprise an about 10 to 20 nm thick silica shell or coating; or the silica coating comprises silica nanoparticle aggregates with the nanoparticle size of about 1, 2, 3, 4, 5, 6, 7, 8, 9, 10, 11, 12, 13, 14, or 15 or more nm in diameter.

In alternative embodiments, the product of manufacture, nanodevice and/or nanosphere of the invention comprises:

(a) a two-phase-nanocomposite coating comprising a metal-containing polymer and/or a bio-degradable polymer;

(b) the nanosphere of (a), wherein the bio-degradable polymer comprises a glycolic acid and/or an ∝-hydroxy acid;

(c) the nanosphere of (b), wherein the polymer layer comprises a bio-degradable polymer layer containing (comprising) pre-mixed metal, oxide, or polymer nanoparticles; or (d) the nanosphere of (c), wherein the metal or oxide particles comprise Ni, Cu, Co and/or Fe oxide particles, or polymer nanoparticles, and a plurality of nanopores is created on the surface by chemical or acid etching of the etchable metal, oxide or polymer nanoparticle composition.

The invention provides products of manufacture comprising a magnetically switchable nano-reservoir array comprising a plurality of magnetically switchable or latchable valves or lids controlling the movement of compositions and/or fluids from within a nano-reservoir positioned below each magnetically switchable or latchable valve or lid with the body of the array. In alternative embodiments, the surface of the array is coated with a chemically inert or a biocompatible film, or a composition comprising gold (Au), platinum (Pt), palladium (Pd) and/or their alloys. In alternative embodiments, the nano-reservoirs are fabricated by DUV (deep UV) lithography or by nano-imprint lithography. The nano-reservoirs can average a nano-reservoir cavity of between about 10 and 1000 nm, or between about 20 and 100 nm, in diameter; or an equivalent average dimension in a square, a rectangle, or a random configuration.

In alternative embodiments, products of manufacture of the invention comprise a plurality of magnetically switchable or latchable valves or lids comprising a stainless steel type magnetic alloy that is remotely triggerable with a pulse magnetic field. The nano-reservoir array can comprise a patterned nano-depot array comprising a flat base magnetic alloy layer with a pre-stressed or pre-bent magnetic alloy cantilever with square-loop magnetics.

In alternative embodiments, the valve or lid of the nano-reservoir cavity can be made of (comprises): (a) square M-H loop magnetic materials with switchable coercivity; (b) a magnetic layer approximately 10 to 100 µm thick; (c) a deposited magnetic film layer or a magnetic layer comprising a lamination bonded thin sheet; or, (d) a magnetic layer that is magnetic field annealed or deformation aged to induce in-plane square M-H loop characteristics with "latchability" to maintain switch closed or open position indefinitely without applying a electrical or magnetic power. The valve or lid of the nano-reservoir cavity can be further coated with a bio-inert material, a gold (Au), a Pt, a Pd and/or their alloys, a polymer and/or PEG (polyethylene glycol).

In alternative embodiments, the nano-reservoirs are filled with (comprises) a chemical, a biological compound, a particle, a cell, or a component of a cell; and in one embodiment, not all nano-reservoirs of a particular product of manufacture (e.g., device, array) have the same compound and/or cell, but can be design to have contained within different reservoirs different compounds or cells that are triggered for release by different mechanisms.

In alternative embodiments, a compound contained within a composition of the invention (e.g., a nanosphere, a product of manufacture, an array) comprises a drug or pharmaceutical composition, an antibiotic, a biological agent, a chemical, a drug, a tracer or marker, or an inorganic nanoparticle, or the cell comprises a mammalian or a human cell, or a bacterial or a yeast cell. The tracer or marker can comprise a quantum dot or a fluorescent dye, a luminescent image tracer or marker, a nuclear medicine imaging tracer or marker, a positron emission tomography (PET) imaging compound, a 18-fluorodeoxyglucose, e.g., a [18F]-2-fluoro-2-deoxyglucose, 6-[$^{18}$F]-fluoro-L-dopa (FDOPA), or a [18F]-3'-fluoro-3'-deoxythymidine. The compound or drug can comprise a biologic, an antibody, a humanized therapeutic antibody, an insulin, a cytokine or a hormonal protein, a steroid, a dexamethasone, an anti-inflammatory or an immunosuppressant steroid, a cancer therapy compound, a paclitaxel (TAXOL™), a mitotic inhibitor drug used in cancer chemotherapy, a 1,3-bis(2-chloroethyl)-1-nitrosourea (BCNU), a radioactive isotope, a polysaccharide, a nucleic acid or a vector or plasmid.

The invention provides devices for diagnosing, treating, preventing or ameliorating a disease or condition comprising (a) the product of manufacture or nanodevice of the invention, the hollow nanosphere of the invention, or the product of manufacture of the invention;
(b) the device of (a), wherein the product of manufacture, nanodevice or nanosphere comprises or is contained within an intradermal or a subcutaneously transplantable assembly, or comprises or is contained within an intravenous formulation; or
(c) the device of (a) or (b), wherein the disease or condition is inherited hemophilia, or Factor VIII or Factor IX deficiency, or a deficient or defective clotting factor or blood-coagulation, or liver function loss because of an infectious disease, hepatitis, or cancer or poisoning, or toxicity or poisoning by insecticides or nerve gas, or the disease or condition is $\alpha_1$ anti-trypsin deficiency in an individual, of a hereditary disease, or a liver disease, or neonatal jaundice and/or emphysema, or the disease or condition is detoxification of blood in patients or an individual having a hereditary disease or condition, or a liver disease or OTC deficiency, or renal insufficiency or uremic poisoning.

The invention provides anti-nerve agent devices, which can be remotely switchable, comprising
(a) the product of manufacture or nanodevice of the invention, the hollow nanosphere of the invention, or the product of manufacture of the invention; or
(b) the anti-nerve agent device of (a), wherein the product of manufacture, nanodevice or nanosphere comprises or is contained within an intradermal or a subcutaneously transplantable assembly.

The invention provides methods for switchable, or controlled "on-off" release of a compound in vivo or in situ, and/or for controlling the movement of a compound-delivering product or device in vivo or in situ, comprising
(i) (a) providing the product of manufacture or nanodevice of the invention, the hollow nanosphere of the invention, or the product of manufacture of the invention;
(b) administering the product of manufacture, nanodevice or nanosphere of (a) to an individual;
(c) applying a magnetic field or an ultrasound wave to an area of the individual in an amount sufficient to cause: (A) local heating and heating of the product of manufacture, nanodevice or nanosphere to a degree sufficient to cause a temperature rise or magnetic stiffing and/or mechanical vibration of a magnetic or ultrasonic responsive particle and/or nanoparticle contained therein, and/or (B) movement of the product of manufacture, nanodevice or nanosphere to the area of the body where the magnetic field is applied;
(ii) the method of (i), wherein the magnetic field or ultrasound wave is applied to the individual in a periodic, or on-off pattern, thereby controlling the release of a compound or cell from the product of manufacture, nanodevice or nanosphere of (a);
(iii) the method of (i), wherein the magnetic field or ultrasound wave is applied to or directed to near an area of the individual needing delivery of a compound or cell, thereby controlling the location of the release of the compound or cell from the product of manufacture, nanodevice or nanosphere of (a);
(iv) the method of (ii) or (iii), wherein the magnetic field or ultrasound wave is applied to the individual in a programmed manner, or with a regimen-controlling mode with patient's response to drug administration coordinated for reprogramming of the regimen, thereby controlling the optimized release of a compound or cell from the product of manufacture, nanodevice or nanosphere of (a);
(v) the method of (iv), wherein the magnetic field or ultrasound wave is applied to the individual having a plurality of the product of manufacture or nanodevice of the invention, or the hollow nanosphere of the invention, or the product of manufacture of the invention, of (a), wherein each or a subset thereof is independently, selectively and/or sequentially activated to administer a chosen combination of different compounds at a chosen release time and/or frequency for each;
(vi) the method of (v), wherein the compounds comprise a drug or a biological agent;
(vii) the method of and of (iv) to (vi), wherein the magnetic field or ultrasound wave applied and the compound selected for release are designed and/or selected to treat a cancer patient.

In one embodiment of a method of the invention, the nano-reservoirs of the nanodevices or nanosphere are filled with (comprise) the identical or different types of a compound and/or a cell. The compound can comprise a drug or pharmaceutical composition, a biological agent, a chemical, a drug, a tracer or marker, or an inorganic nanoparticle, or the cell comprises a mammalian or a human cell, or a bacterial or a yeast cell. The tracer or marker can comprise a quantum dot or a fluorescent dye, a luminescent image tracer or marker, a nuclear medicine imaging tracer or marker, a positron emission tomography (PET) imaging compound, a 18-fluorodeoxyglucose, e.g., a [18F]-2-fluoro-2-deoxyglucose, 6-[$^{18}$F]-fluoro-L-dopa (FDOPA), or a [18F]-3'-fluoro-3'-deoxythymidine. The compound or drug can comprise a biologic, an antibody, a humanized therapeutic antibody, an insulin, a cytokine or a hormonal protein, a steroid, a dexamethasone, an anti-inflammatory or an immunosuppressant steroid, a cancer therapy compound, a paclitaxel (TAXOL™), a mitotic inhibitor drug used in cancer chemotherapy, a 1,3-bis(2-chloroethyl)-1-nitrosourea (BCNU), a radioactive isotope, a polysaccharide, a nucleic acid or a vector or plasmid.

In alternative embodiments of the methods, ultrasonic waves are applied to a focused area of the individual in an amount between about 20 KHz to 10 MHz, or an amount between about 200 KHz to 2 MHz. In one aspect, a radio frequency (RF) magnetic field is applied to a focused area of the individual. In one aspect, an external AC magnetic field is applied to a focused area of the individual in an amount sufficient to induce a localized temperature rise (increase) within the product of manufacture, nanodevice or nanosphere. The external AC magnetic field can be about 100 KHz, or is between about 50 and 250 KHz.

In alternative embodiments of the methods, a slow change of gradient field direction is applied to a focused area of the individual to induce a vibrational movement of magnetic nanoparticles within the product of manufacture, nanodevice or nanosphere, and/or to induce localized liquid pressure variations within the nanosphere.

In alternative embodiments of the methods, about 1 to 100 Hz frequency and about 0.1 to 5 KG magnetic field is applied to a focused area of the individual.

In alternative embodiments of the methods, a sufficient amount of RF or external AC magnetic field or ultrasound (ultrasonic wave) is applied to a focused area of the individual to induce (make) the magnetic or non-magnetic particles within the product of manufacture, nanodevice or nanosphere vibrate, thereby enhancing compound or cell release from the product of manufacture, nanodevice or nanosphere while the RF or external AC magnetic field, or ultrasonic wave, is applied to the individual.

In alternative embodiments of the methods, a multiplicity of external electromagnets or rotating permanent magnets are arranged around the individual and operated in such a way that an alternating or sequential magnetic field is applied in an amount sufficient to induce a lateral (vibrational) movement of a nanoparticle and/or the compound within the product of manufacture, nanodevice or nanosphere.

In alternative embodiments of the methods, a sufficient amount of a laterally oscillating gradient field with alternating magnetic field directions is applied the individual to induce magnetic particles within the product of manufacture, nanodevice or nanosphere to move and/or vibrate.

In alternative embodiments of the methods, a sufficient amount of RF heating and/or pressure-gradient-based mechanisms applied the individual to induce a particle movement within the product of manufacture, nanodevice or nanosphere via a low frequency, direction-changing field.

In alternative embodiments of the methods, a DC magnetic gradient field applied the individual to induce a movement of the product of manufacture, nanodevice or nanosphere toward the desired location of drug or compound release. In alternative embodiments of the methods, a magnet with a surface field strength of at least about 100 Oe, or at least about 1,000 Oe, or at least about 3,000 Oe, is applied to the individual such that the product of manufacture, nanodevice or nanosphere responds and moves toward the direction of the gradient magnetic field.

In alternative embodiments of the methods, the magnetic field or ultrasound wave is applied to or directed to the central nervous system (CNS), thereby controlling the location of the release of the compound or cell from the product of manufacture, nanodevice or nanosphere of (a) to cross the blood brain barrier (BBB) and enter the CNS.

In alternative embodiments of the methods, a magnetic field or ultrasound wave that activates the release of the compound or cell from the product of manufacture, nanodevice or nanosphere of (a) is applied to or directed to an area of the individual only after the product of manufacture, nanodevice or nanosphere of (a) has been directed to and has reached that area of the individual.

In alternative embodiments of the methods, a magnetic field or ultrasound wave that activates the release of the compound or cell from the product of manufacture, nanodevice or nanosphere of (a) is applied to or directed to the CNS only after the product of manufacture, nanodevice or nanosphere of (a) is directed to cross the blood brain barrier (BBB) and has entered the CNS.

The details of one or more aspects of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF THE DRAWINGS

The advantages, nature and additional features of the invention will appear more fully upon consideration of the illustrative embodiments described in the drawings of the invention. The following drawings are illustrative of aspects of the invention and are not meant to limit the scope of the invention as encompassed by the claims.

FIG. 2(a) illustrates a laterally oscillating gradient field with alternating magnetic field directions to induce magnetic particle movement and vibration; FIG. 2(b) illustrates sequentially actuated electromagnetic for rotating field; FIG. 2(c) illustrates use of ultrasound signal to vibrate both the magnetic nanoparticles and the capsule shell for activation of compound (e.g., drug, tracer) release; as described in detail below.

FIG. 3(a) illustrates ferromagnetic nanoparticles comprising biocompatible particles; FIG. 3(b) illustrates coating a metal layer; FIG. 3(c) and FIG. 3(e) illustrate chemically etching away the coating (complete or partially etched, FIG. 3(c) and FIG. 3(e), respectively); and in FIG. 3(d) and FIG. 3(f), the hollow reservoir space is filled with desired compositions (e.g., drugs, tracers and the like), as discussed in detail, below.

in FIG. 4(b)(a) magnetic nanoparticles such as $Fe_3O_4$ nanoparticles are coated as in FIG. 4(b)(b) with a shell of Au, silica polymer or graphite with a second phase material or particles, followed by generation of nanopores as in FIG. 4(b)(c), and trapping of a magnetic particle as in FIG. 4(b)(d) and a composition (e.g., a drug) to be released as in FIG. 4(b)(e), as discussed in detail, below.

FIG. 9(a) illustrates a low magnified image, and FIG. 9(b) a high magnified image, as discussed in detail, below.

FIG. 10(a) graphically illustrates data demonstrating enhanced drug release in water by 100 KHz magnetic RF field for 2 minutes; FIG. 10(b) graphically illustrates data demonstrating cyclic on-off switched drug release by magnetic field control, as discussed in detail, below.

FIG. 14 illustrates images of exemplary $Fe_3O_4$ nanoparticles with: FIG. 14(a) 2 nm, FIG. 14(b) 6 nm, FIG. 14(c) 15 nm diameter pores, e.g., a drug to be released, as discussed in detail, below.

FIG. 15(a) illustrates the BBB crossing of nanoparticles of the invention using magnetic gradient field and subsequent composition (e.g., tracer, drug) release by remote RF field and/or ultrasonic activation in the intended brain location, FIG. 15(b) illustrates magnetic position fixing of accumulation of nanoparticles of the invention (e.g., drug capsules) and subsequent composition (e.g., tracer, drug) release by RF field or ultrasonic activation, as discussed in detail, below.

FIG. 16(a) illustrates a patterned nano-depot array comprising a flat base magnetic alloy layer with a pre-stressed (e.g., pre-bent) magnetic allow cantilever with square-loop magnetics, illustrating exemplary valve #1 and valve #2 releasing a drug; the illustration shows a valve open with the magnetic base and the magnetic cantilever demagnetized; FIG. 16(b) illustrates the array of FIG. 16(a) but with the valves closed when the magnetic components are magnetized; FIG. 16(c) illustrates exemplary silicon (Si) nano-patterned cavity arrays having 160 nm and 320 nm diameter cavities, as discussed in detail, below.

FIG. 17(a) graphically illustrates how a DC pulse field fully magnetizes, while a gradually diminishing AC field cycles demagnetizes (noting the latched remnant magnetization after pulsing by a pulse field of 1 msec, and demagnetization by AC current to a zero magnetic moment); FIG. 17(b) illustrates a TEM of a Fe—Cr—Co stainless steel magnet spinodally decomposed into two-phase microstructure; FIG. 17(c) illustrates a TEM of the Fe—Cr—Co stainless steel magnet of FIG. 17(b) after deformation elongated to induce shape-anisotropy, as discussed in detail, below.

FIG. 20(a) illustrates an exemplary press nano-imprint stamp pressed into an exemplary spin-coated PDMS (containing magnetic particles), which is illustrated as being cured by UV light and/or heating; FIG. 20(b) illustrates release (withdrawal) of the stamp; FIG. 20(c) illustrates a TEM of an exemplary nano-imprint stamp of the invention comprising a protruding, pin-head type pillar array; and FIG. 20(d) illustrates a TEM of an exemplary PDMS nano-imprinted pattern with an equi-diameter pillar array nano-stamp, as discussed in detail, below.

It is to be understood that the drawings are for purposes of illustrating the concepts of the invention and are not to scale.

Like reference symbols in the various drawings indicate like elements.

DETAILED DESCRIPTION

The invention provides nanodevices or products of manufacture for use as compound delivery vehicles, e.g., as drug or diagnostic visualization delivery vehicles. In one aspect, the invention provides nanodevices or products of manufacture having on-off release mechanisms for compounds contained therein, e.g., for use as drug delivery nano-vehicles having on-off drug or biological agent release mechanisms, and their therapeutic applications. Biological agents that can be stored in the nanostructure devices and products of manufacture of this invention include cells, growth factors, collagens, various proteins/biomolecules, genes, enzymes, hormones, DNAs, antibiotics, drugs, and functional nanoparticles. The nanodevices or products of manufacture of the invention can comprise any desired material, composition or agent, e.g., cells, drugs, growth factors, hormones, proteins, enzymes, antibiotics, antibodies, DNA, nanoparticles, vitamins and minerals, air fresheners, gas-generating compounds (such as for oxygen, nitrogen, air, ozone or chlorine), or any chemicals.

In one aspect, the invention provides medical treatments and medical imaging compounds and methods, including drug therapy, using nanodevices or products of manufacture to restore normal functioning conditions of physiological homeostasis in human body. A compound (e.g., drug, tracer, small molecule) or cell contained in a nanodevice or product of manufacture of the invention can be a chemical compound, a protein, a hormone, or a live cell, including a mammalian cell.

Compounds (e.g., drugs) contained in a nanodevice or product of manufacture of the invention can be delivered by any means, e.g., through oral doses, inhalation sprays, intraocularly, intravascularly (e.g., intravenously, as by injection), intramuscular injection, topically (as on the mucosa or skin), intradermal, intrathecal or from implanted devices.

For efficient use of compounds (e.g., drugs) where a certain desired therapeutic concentration range is desired to be, or must be, maintained (e.g., as they become ineffective at low levels and are often toxic beyond certain concentrations) the nanodevices or products of manufacture are used for controlled release. In one aspect, not all of a dosed drug or other compound (e.g., in nanodevices or products of manufacture of the invention) is delivered to a target, e.g., a targeted organ. Thus, in one aspect, the practicing the invention avoids administrations of a large excess of compound (e.g., drug) to make a small amount of compound actually available for the needed therapeutics, which results in deleterious side effects and can also contribute to drug addiction and abuse.

Figure 1:
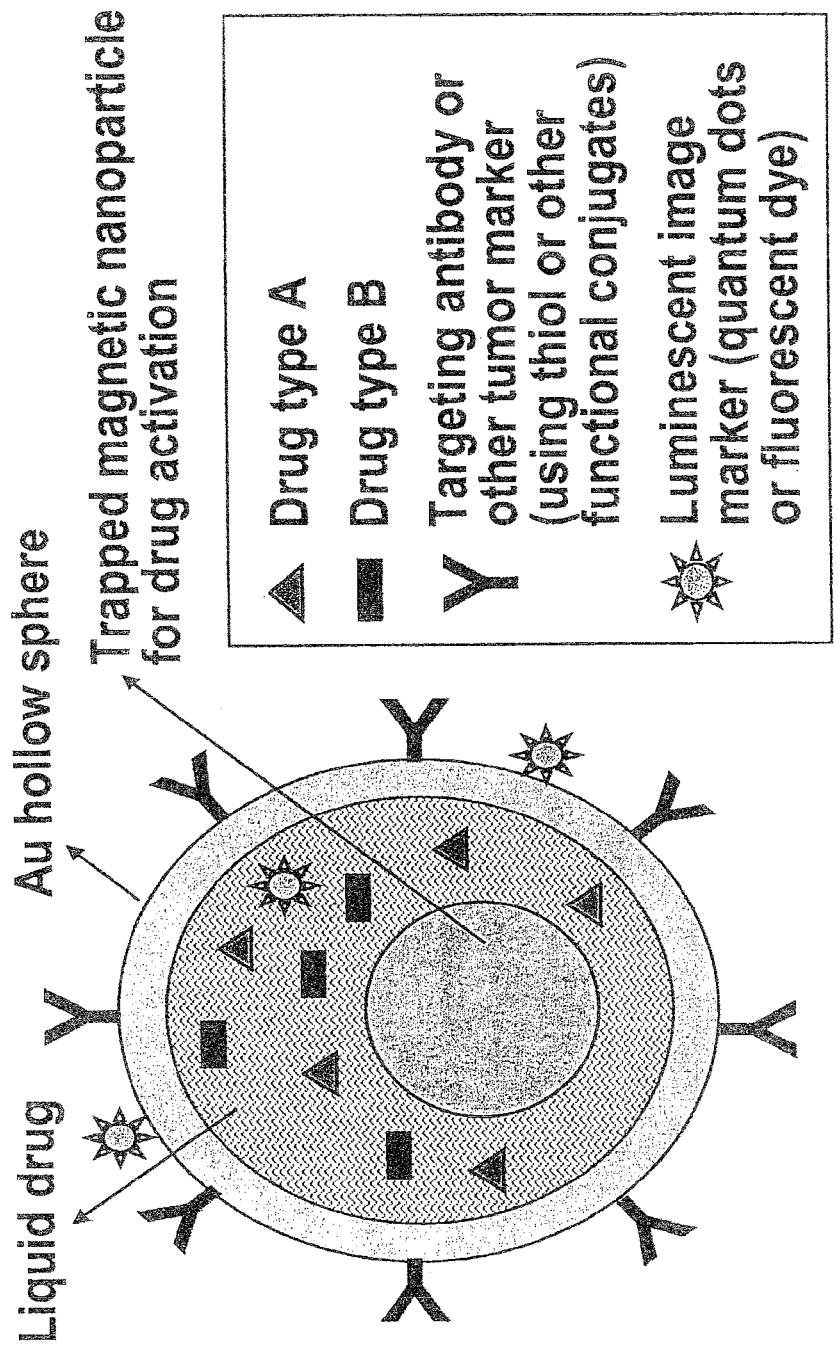
FIG. 1 illustrates an exemplary hollow multifunctional nanosphere of the invention having as compounds contained therein at least two different compounds, e.g., a particulate drug and a liquid drug, a targeting antibody (e.g., to target a specific cell, tissue or organ), and a luminescent image marker (e.g., a quantum dot or a fluorescent dye); as described in detail below.

One exemplary embodiment comprises hollow multifunctional nanospheres with magnetically or ultrasonically triggerable compound (e.g., drug, biologic, tracer and the like) release, as illustrated in FIG. 1; e.g., the invention provides in one exemplary aspect a multifunctional biocompatible semi-hollow nanospheres with remote triggerable release of compound stored inside. For example, in FIG. 1 illustrates an exemplary hollow multifunctional nanosphere of the invention having as compounds contained therein at least two different compounds, e.g., a particulate drug and a liquid drug, a targeting antibody (e.g., to target a specific cell, tissue or organ), and a luminescent image tracer or marker (e.g., a quantum dot or a fluorescent dye). In one aspect, the targeting antibody is attached to the surface of the nano sphere using a thiol or other functional conjugate.

In an alternative embodiment, the semi-hollow nanosphere of the invention also incorporates a conventional compound (e.g., drug) delivery approaches, e.g., attaching a compound, e.g., a drug, tracer or other molecule, onto the surface of nanoparticles through functionalization and conjugation with proteins and other biomolecules. However, this tends to increase the overall diameter of the compound (e.g., drug) delivery vehicles, thus making it more difficult to move around to target the intended organ location for compound (e.g., drug) delivery. An example of such a difficulty is for intended compound (e.g., drug) delivery by crossing the brain-blood barrier through the tight gap junctions or through endocytosis. The movement and heating of magnetic nanoparticles are severely deteriorated if the overall diameter is increased by polymer conjugation as a strong dependence on the size and the suspending medium is observed. Thus, in another alternative embodiment, nanospheres of the invention only contain compound, e.g., a drug, tracer or other molecule, inside the nanosphere—and the compound's release from the inside of the nanosphere is triggerable. One embodiment comprises a nanosphere of the invention as a compound (e.g., drug) delivery vehicle design that is compact in nature; the compound (e.g., drug) is stored and carried within the nanospheres, thus the overall size is relatively small (is much smaller than if the nanosphere has compound, e.g., a drug, tracer or other molecule, outside of the nanosphere.

Instead of regular hollow spheres for compound (e.g., drug) storage and slow release, this embodiment of invention fabricates and utilizes a triggerable, bio-inert or biocompatible nanospheres which contain a remote-actuatable material inside, notably magnetic nanoparticles responsive to external radio frequency (RF) magnetic field (a magnetic field generated from an RF source) as illustrated in FIGS. 1 through 5. In one aspect, an external AC magnetic field (e.g., 100 KHz, or in the range of between about 5 KHz to 5 MHz) induces localized temperature rise within the nanosphere; in one aspect, the compositions and methods of this invention provide for magnetic nanoparticle heating for magnetic hyperthermia treatment, e.g., of cancer or other dysfunctional cells, e.g., as described in references 17, 18, below.

In one aspect, an alternative mechanism of compound (e.g., drug) release on-demand comprises magnetic movement of particles (which can be done e.g., as described in reference 18, below) and stiffing within the nanosphere; in one aspect accelerated compound (e.g., drug) delivery occurs when effectuating a slow change of gradient field direction (e.g., about 1 to 100 Hz frequency and about 0.1 to 5 KG magnetic field) to induce a vibrational movement of the trapped magnetic nanoparticle and localized liquid pressure variations within the sphere.

Another alternative embodiment comprises utilizing ultrasonic agitation which can also make the particles (either magnetic or non-magnetic) to vibrate and enhance compound (e.g., drug) release while the ultrasonic wave is applied to a person's body.

As illustrated in FIG. 1, the first embodiment of the invention relates to multi-functional hollow spheres which contain intentionally trapped magnetic nanoparticle(s), stored drugs to be delivered, plus optionally luminescent particles such as quantum dots or fluorescent dyes for imaging/diagnosis purposes. On the outside shell surface such as bio-inert gold (Au) or silica shells, tumor markers and additional image markers can be conjugated for targeted drug delivery using thiol interactions, peptide conjugates or antibody-antigen conjugation approaches.

Nanotechnology based delivery of CNS (Central Nervous System) therapeutic drugs such as by using antibody targeting mechanism may offer a unique possibility of overcoming the blood-brain barrier that prevents access of drugs to important brain regions, thus allowing easier treatment of neurological diseases such as epilepsy, Alzheimer's disease, schizophrenia, multiple sclerosis, and brain tumors.

Figure 2:
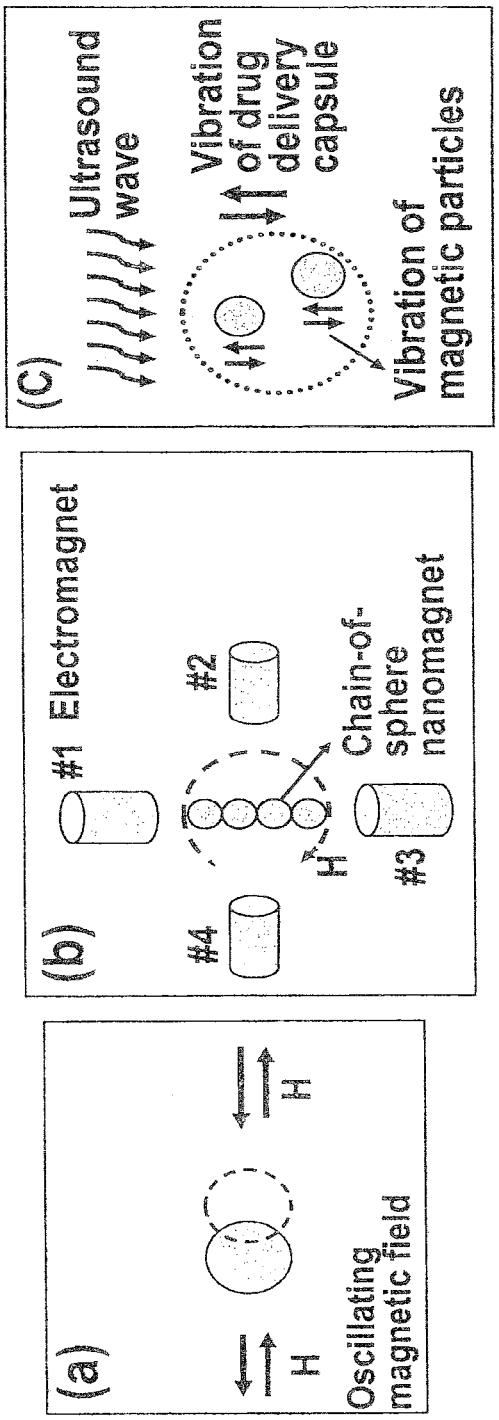
FIG. 2 illustrates exemplary means for application of external signals for drug delivery actuation.

This embodiment of the invention is schematically illustrated in FIG. 2. In this embodiment, a multiplicity of external electromagnets or rotating permanent magnets are arranged and operated in such a way that an alternating or sequential magnetic field is applied, which induces lateral (vibrational) movements, as illustrated in FIG. 2(a), or rotational movement, as illustrated in FIG. 2(b), of the magnetic nanoparticles within the hollow capsule. In FIG. 2(b), exemplary electromagnet elements #1, #2, #3 and #4 induce movement of a "chain-of-sphere" nanomagnet of a composition of the invention.

An alternative embodiment to activate the drug release is to use remotely applied ultrasonic waves to generate the motion and vibration, as illustrated in FIG. 2(c), of the capsule containing a composition to be delivered (e.g., a drug or tracer) and magnetic nanoparticles. In alternative embodiments, the frequency of such ultrasonic waves is in the range of between about 20 KHz to 10 MHz, e.g., in the range of 200 KHz to 2 MHz. In this embodiment, mechanical motion and vibration of the magnetic particles are the main mechanism of compound (e.g., drug, tracer) release. Since the ultrasound waves will also vibrate the capsules themselves, the compound (e.g., drug, tracer) release is further enhanced by the ultrasound.

In summary, FIG. 2 illustrates exemplary means for application of external signals for drug delivery actuation: FIG. 2(a) illustrates a laterally oscillating gradient field with alternating magnetic field directions to induce magnetic particle movement and vibration; FIG. 2(b) illustrates sequentially actuated electromagnetic for rotating field; FIG. 2(c) illustrates use of ultrasound signal to vibrate both the magnetic nanoparticles and the capsule shell for activation of compound (e.g., drug, tracer) release.

Figure 3:
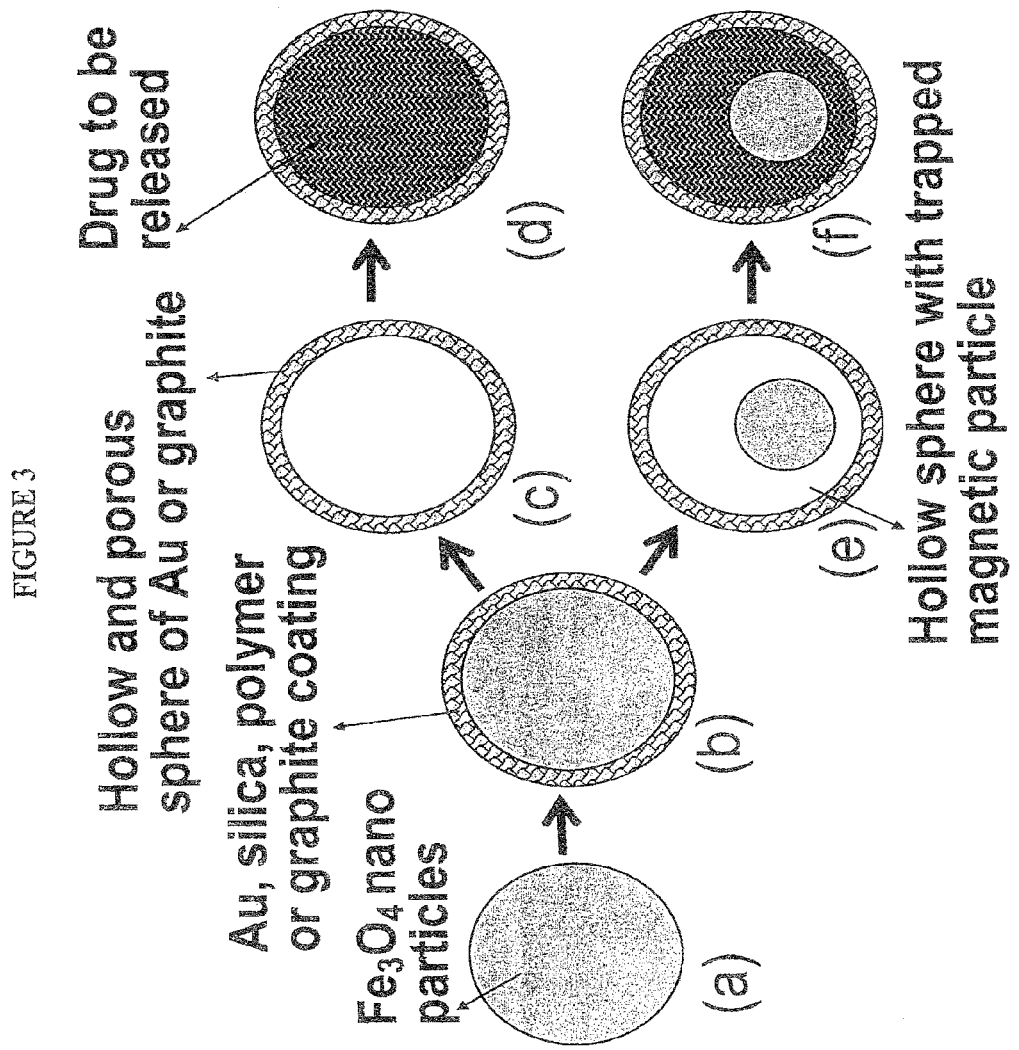
FIG. 3 schematically illustrates a sequence of proposed procedures for fabricating exemplary hollow drug delivery vehicles of the invention.

FIG. 3 schematically illustrates a sequence of proposed procedures for fabricating exemplary hollow drug delivery vehicles of the invention which are imparted with remotely-switchable delivery capability. Ferromagnetic nanoparticles, as illustrated in FIG. 3(a), e.g., which can comprise the well known and biocompatible $Fe_3O_4$ (magnetite), $Fe_2O_3$ (maghemite) particles, are first coated with a metal layer (such as Au, Pt, stainless steel, or alloys), ceramics (such as silicon oxide, aluminum oxide, titanium oxide), carbon or carbide (such as graphite, Ti-carbide, Zr-carbide, Si-carbide), or polymer, by various known deposition techniques (as illustrated in FIG. 3(b), including e.g. chemical precipitation, sol-gel synthesis, displacement reactions, electroless deposition, electrochemical deposition (if a rotating electrode is used), chemical or physical vapor deposition inside a fluidized bed. An annealing heat treatment of coated particles on the spheres may optionally utilized. Such post-deposition annealing at various atmospheres is often beneficial as it can enhance the consolidation of the shell material for enhanced mechanical ruggedness and introduce desired nano-pores by partial sintering shrinkage in the shell material. Thermal expansion mismatch of the shell material with the core material, or partial burning of the polymer on high temperature annealing treatment may also contribute to the nano-pore formation. In one embodiment, such nano-pores are needed for composition (e.g., drug) release. The interior magnetic material is then chemically etched away either completely as illustrated in FIG. 3(c) or partially etched as illustrated in FIG. 3(e); which in some embodiments can be more desirable for a controlled composition (e.g., drug) delivery mechanism. The hollow reservoir space is then filled with desired compositions (e.g., drugs, tracers and the like), as illustrated in FIG. 3(d) and FIG. 3(f).

In summary, FIG. 3 illustrates an exemplary fabrication of the invention comprising remotely on-off switchable, hollow or semi-hollow composition (e.g., drug) delivery vehicles. Alternative embodiments of the invention comprise another alternative way of forming nanoporous shell structure: using a dual-phased or composite material coating on magnetic core particle followed by selective etching, as schematically illustrated in FIG. 3. For gold (Au) or platinum (Pt) type metals, a more easily etchable metals such as copper (Cu) or nickel (Ni) may be added on the surface of the magnetic core (FIG. 3(a)) as an alloy coating, or two-phase, precipitate-containing phase coating, or composite mixed-particle coating (FIG. 3(b)). Subsequent chemical etching preferentially removes the more etchable metal or precipitate and produces a nanoporous shell (FIG. 3(c)). If a polymer base material is used, a co-polymer coating can be used followed by selective dissolution of one of the phases. A mixed polymer coating, on carbonization or graphitization by high temperature pyrolysis, can also be made into a nanoporous shell of carbon or graphite. The core-shell particles with nanoporous shell are then chemically etched for desirable duration of time so that the core magnetic particles are only partially etched (FIG. 3(d)) to allow filling of the remaining space with drug(s) or biological agent(s) as illustrated in FIG. 3(e).

In one aspect, the hollow shell material is chosen to be Au, and for this aspect of the invention the exemplary hollow composite systems as illustrated in FIG. 1 and FIG. 2(f) enable more powerful, multi-functional therapeutics:

In one embodiment the invention provides on-demand composition (e.g., drug) release and positioning: (i) On-off releases composition (e.g., drug) at will, and/or ii) Provides magnetic maneuverability; e.g. as described in reference 19, below.

In one embodiment the invention provides dual magnetic imaging and therapeutics and diagnostics: (i) Magnetic particle can be RF heated for magnetic hyperthermia, e.g., for the treatment of a cancer; e.g. as described in reference 20, below, and/or ii) Enhanced magnetic MRI and/or PET imaging.

In alternative embodiments the invention provides dual optical imaging and therapeutics and diagnostics: (i) a gold (Au) nanoshell allows enhanced imaging/cancer detection; e.g. as described in references 16, 21, 22, 23, as listed below; and/or ii) a gold (Au) nanoshell also allows photothermal treatments, e.g., as cancer treatment; e.g. as described in references 22, 23, below.

In one embodiment, the invention provides hollow spheres with stored magnetic particles for "on-off" controlled composition (e.g., drug) release, which can be utilized for targeting to a desired tissue or organ (such as a cancer region) using various types of conjugations. Both gold (Au) and silica shells in exemplary hollow spheres can be conjugated with antigen-antibody and various other means for targeting to the desired organ sited, for example, by blood circulation or injection to near the target organ regions and subsequent magnetic movement of the hollow particles. In one embodiment, immuno-targeted nanoshells of gold can scatter light for cancer imaging and/or absorb light for selective destruction of targeted carcinoma cells (e.g., breast cancer cells, as described in references 22 and 23, below) through a photothermal therapy.

In alternative embodiments, the invention provides two exemplary approaches for actuate-able drug release from hollow sphere capsules are utilized as described above, and as illustrated further in FIGS. 4 through 6.

Figure 4A:
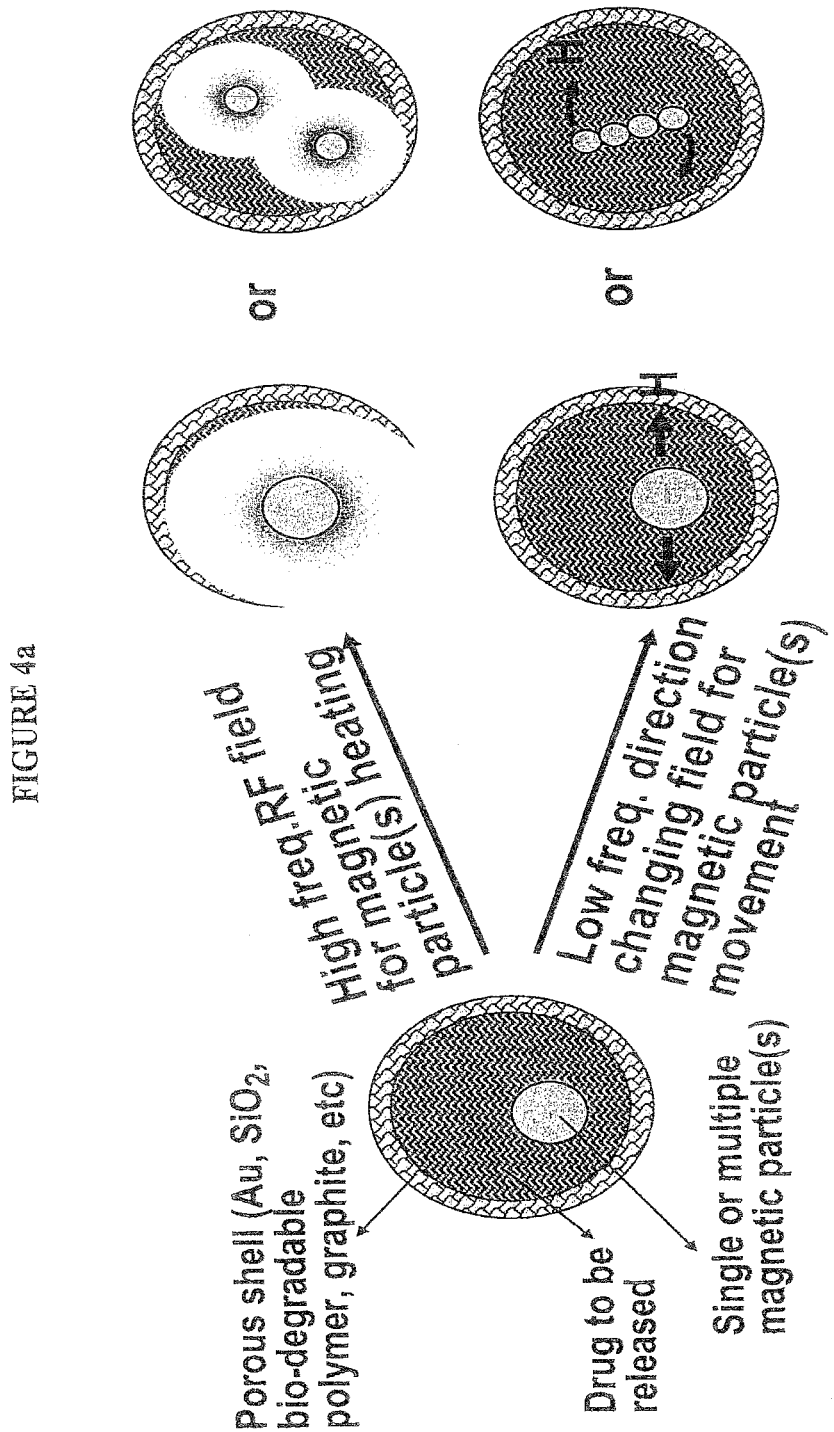
FIG. 4(a) illustrates exemplary temperature-gradient-based composition release compositions and mechanisms of the invention comprising use of RF heating (two upper right diagrams) and/or pressure-gradient-based mechanisms by vigorous particle movement via low frequency, direction-changing field (two lower right diagrams), as discussed in detail, below.

In alternative embodiments, the invention provides remote high-frequency RF magnetic field to selectively heat the hollow shell interior to induce a temperature gradient and induce accelerated drug release. In alternative embodiments, the invention provides remote low-frequency, direction-changing magnetic field to induce magnetic particle movement within the hollow shell and enable accelerated drug release. These two exemplary approaches are schematically illustrated in FIG. 4. The specifics of design of such hollow capsule materials with trapped magnetic nanoparticles depend on which of these two approaches are aimed at, utilizing materials and chemistry processes known to those skilled in the art, FIG. 4(a) illustrates exemplary temperature-gradient-based composition (e.g., tracer, drug) release composition and mechanism of the invention comprising use of RF heating (two upper right diagrams) and/or pressure-gradient-based mechanisms by vigorous particle movement via low frequency, direction-changing field (two lower right diagrams). FIG. 4(a) illustrates an exemplary porous shell nanoparticle of the invention comprising a composition (e.g., a drug) to be released with single or multiple magnetic particles, and optionally having a porous shell of e.g., gold (Au), $SiO_2$, a bio-degradable polymer, a graphite, and the like.

Figure 4B:
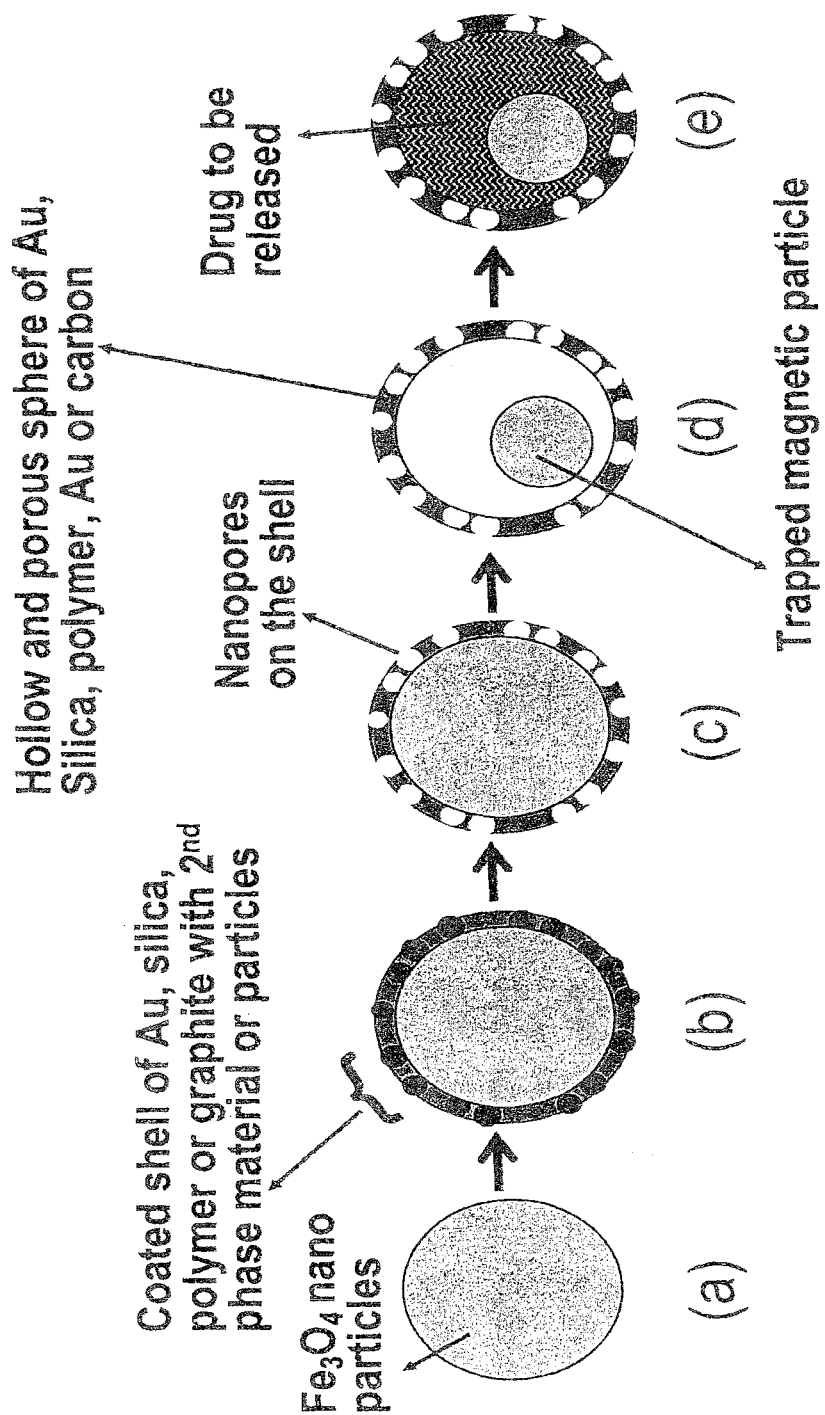
FIG. 4(b) illustrates exemplary silica based hollow nanospheres of the invention.

FIG. 4(b) illustrates exemplary silica-based semi-hollow nanospheres of the invention: in FIG. 4(b)(a) magnetic nanoparticles such as $Fe_3O_4$ nanoparticles are coated as in FIG. 4(b)(b) with a shell of Au, silica polymer or graphite with a second phase material or particles, followed by generation of nanopores as in FIG. 4(b)(c), and trapping of a magnetic particle as in FIG. 4(b)(d) and a composition (e.g., a drug) to be released as in FIG. 4(b)(e).

Alternative embodiments of the invention, including the remote switchable compound—(e.g., tracer-, drug-) release compositions, are described below.

Silica Shell Hollow Spheres with Trapped Magnetic Particle(s)

Figure 5:
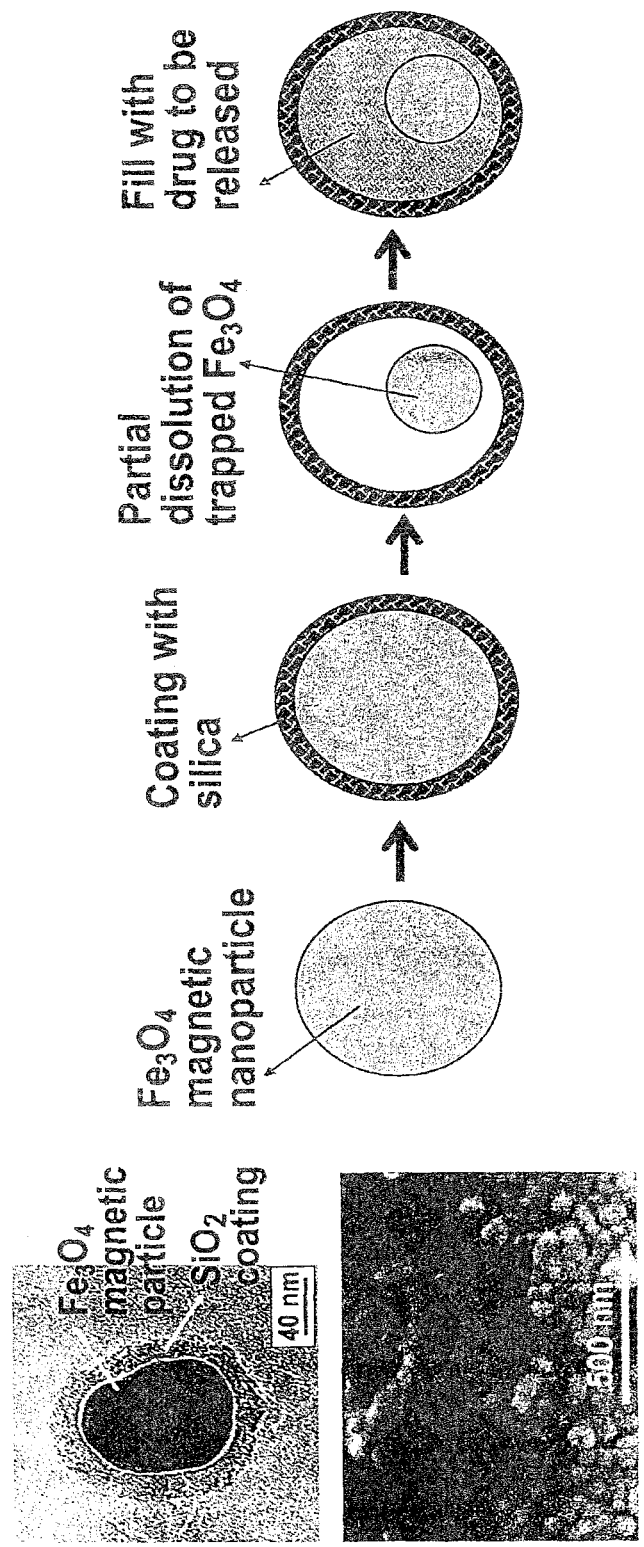
FIG. 5, upper left image, illustrates an exemplary transmission electron micrograph (TEM) of 10 to 20 nm thick silica coating on $Fe_3O_4$ particles with tetraethylorthosilicate (TEOS); an embodiment comprising a lower concentration of silica-containing chemicals with a more nanoparticle-stack type coating is illustrated in the lower left image in FIG. 5; and the right image schematics in FIG. 5 illustrate an exemplary composition of the invention comprising silica shell containing a single trapped magnetic particle and inserted drug: first image is a $Fe_3O_4$ nanoparticle, the second image is the nanoparticle coated with silica, the third image illustrates partial dissolution of the "trapped" $Fe_3O_4$ nanoparticles, and the fourth image illustrated the $Fe_3O_4$ nanoparticle filled with a composition to be delivered in vivo, e.g., a drug, as discussed in detail, below.

A switchable compound—(e.g., tracer-, drug-) release embodiment of the invention comprises a composition comprising a magnetic nanoparticle contained (or "trapped") within a silica shell. This embodiment is schematically illustrated in FIG. 5. In this embodiment, a silica ($SiO_2$) coating of magnetic nanoparticles is useful for providing biocompatibility, and enabling convenient functionalization and conjugation on the outside surface if needed.

An example transmission electron micrograph (TEM) of 10 to 20 nm thick silica coating on $Fe_3O_4$ particles with tetraethylorthosilicate (TEOS) is shown in FIG. 5 upper left image. In alternative embodiments, by utilizing a lower concentration of silica-containing chemicals a more nanoparticle-stack type coating is achieved, an example shown as the lower left image in FIG. 5; which in some embodiments a 3 to 10 nm silica particle diameter regime is used for enhanced nanoporosity. In other embodiments the silica particle is about 1, 2, 3, 4, 5, 6, 7, 8, 9, 10, 11, 12, 13, 14, or 15 or more nm in diameter. The schematics in FIG. 5 (right images) illustrates an exemplary composition of the invention comprising silica shell containing a single trapped magnetic particle and inserted drug: first image is a $Fe_3O_4$ nanoparticle, the second image is the nanoparticle coated with silica, the third image illustrates partial dissolution of the "trapped" $Fe_3O_4$ nanoparticles, and the fourth image illustrated the $Fe_3O_4$ nanoparticle filled with a composition to be delivered in vivo, e.g., a drug.

The following example protocol can be employed for fabrication of such exemplary stacked, more porous silica nanoparticles of the invention utilizing a sol-gel processing: i) Add 5 gram of $Fe_3O_4$ powder (e.g., about 50 to about 200 nm diameter) to 10 ml of Tetra-methyl ammonium hydroxide (TMAH, Aldrich) with mechanical stirring for 30 min. at room temp and centrifuge at 4000 rpm (10 min); ii) Add 0.5 ml of $NH_4OH$ (30 wt % Aldrich) with mechanical stiffing for 10 minutes; iii) Add 100 microliter of Tetraethylorthosilicate (TEOS: Aldrich) with mechanical stirring for about 3 hrs and centrifuge at 4000 rpm (10 min), remove supernatant, and add D.I. water to re-disperse $SiO_2$ coated $Fe_3O_4$ nanoparticle; iv) The silica coated magnetic particle are then placed in 1M HCl for 2-12 hrs to partially dissolve the magnetic particle; and, v) a desired compound to be delivered (e.g., a tracer, a drug) is inserted to the interior of the hollow spheres using a vacuum or diffusion guided processing.

Figure 6:
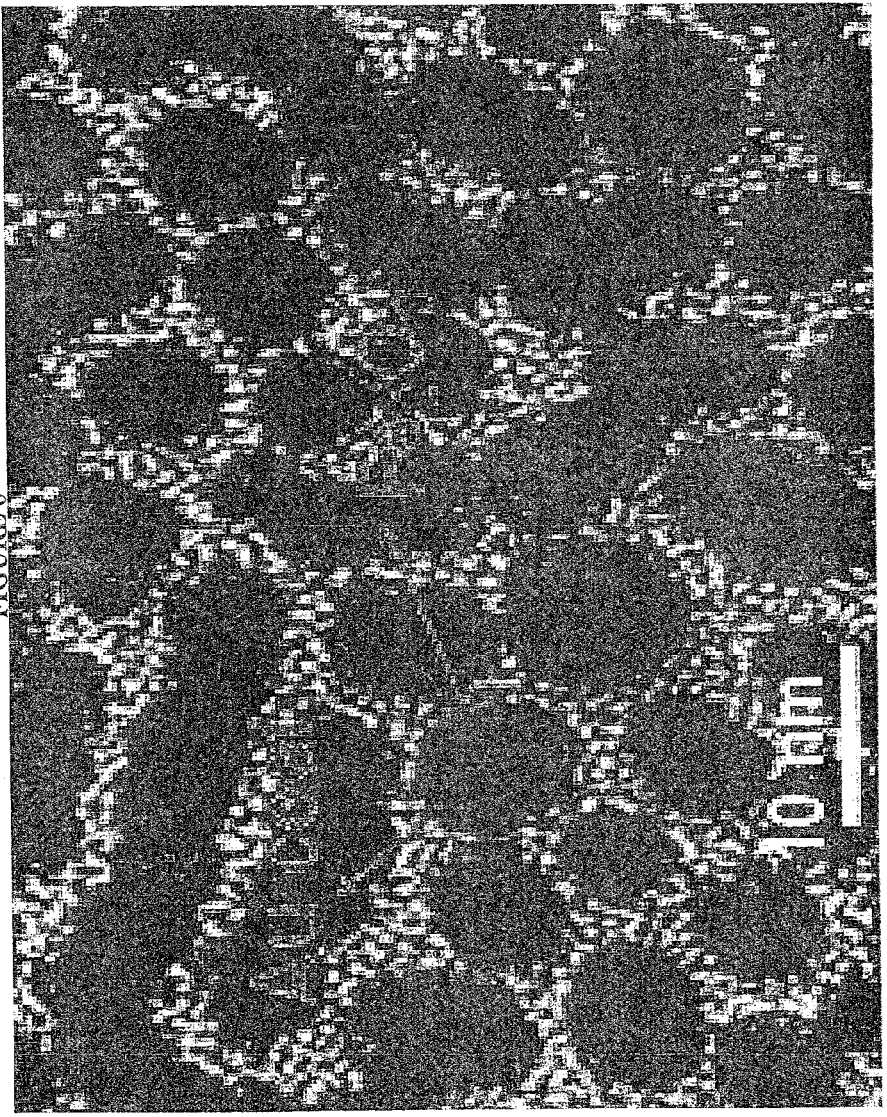
FIG. 6 illustrates a TEM of an exemplary silica-based hollow nanosphere of the invention with a trapped magnetic nanoparticles, as discussed in detail, below.

FIG. 6 illustrates a TEM (transmission electron microscopy) micrograph of an exemplary silica-based gold-(Au—) coated $Fe_2O_3$ magnetic nanoparticles comprising hollow nanospheres with a trapped magnetic nanoparticles, comprising gold (Au) shell hollow spheres with trapped magnetic particle(s). The exemplary gold (Au) nanoshell coating provides a bio-inert surface, and also allows enhanced imaging as well as photothermal cancer treatment. Both gold (Au) and silica shells enable a conjugation with antigen-antibody and various other means for targeting to the desired organ sited. Coating of gold (Au) on magnetic nanoparticles can be obtained using well known protocols to those skilled in the art. An exemplary nanoparticle of the invention comprising few nanometer thick Au-coating on the surface of iron oxide nanoparticles is shown in the TEM micrograph illustrated in FIG. 6. The Au-shell based hollow sphere vehicles with a magnetic particle and a drug to be delivered inside (e.g., illustrated in FIG. 3 or 4) can be fabricated by controlled, partial etching of the magnetic particle trapped within the sphere using acidic solutions as the gold shell is made nanoporous according to the invention.

Silica or Gold Shell Hollow Spheres with Multiple Magnetic Particles Trapped

Figure 7:
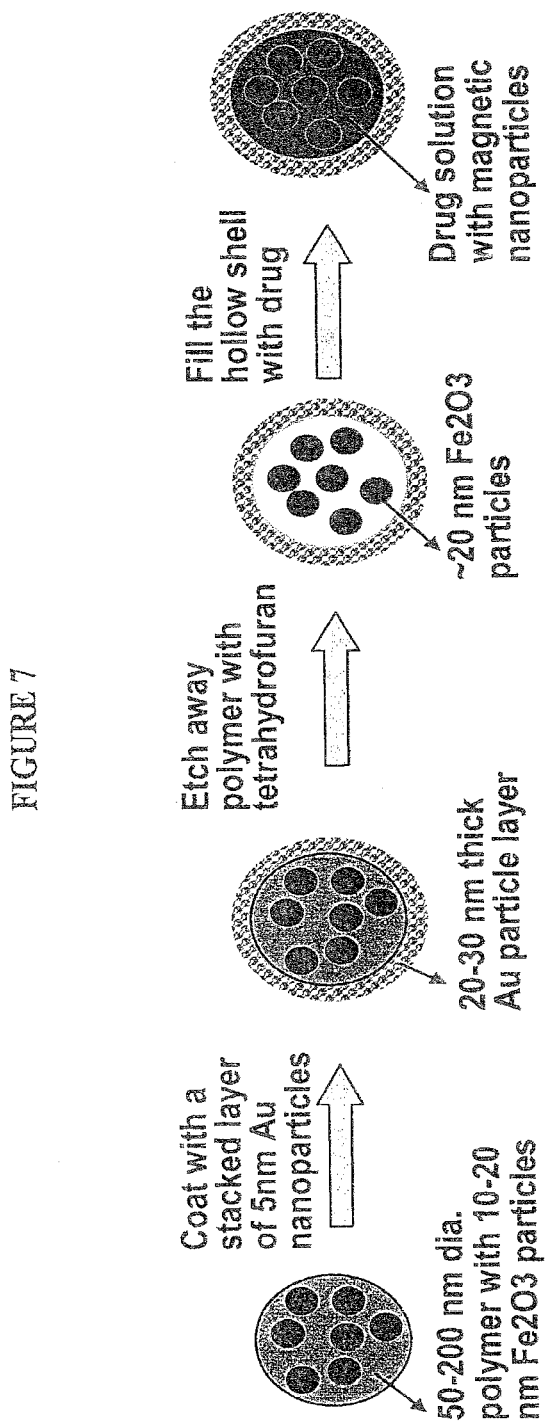
FIG. 7 illustrates multiple magnetic nanoparticles of the invention: the first image illustrates a plurality of magnetic nanoparticles within a 50 to 200 nm diameter (dia) polymer with 10 to 20 nm $Fe_3O_4$ particles, which is coated with a stacked layer of 5 nm Au particles; in the second image a 20 to 30 nm Au particle layer is illustrated, and the polymer is then etched away with e.g., tetrahydrofuran; the third image illustrates a plurality of approximately 20 nm $Fe_3O_4$ particles, and the fourth image illustrates that the hollow-shelled particles are then filled with a compound, e.g., a drug solution, as discussed in detail, below.

In another embodiment, instead of a single magnetic particle, multiple magnetic particles are used (are included) in the interior of a gold (Au) hollow shell, e.g., as illustrated in FIG. 7. In this embodiment, having multiple particles can offer advantages of a more homogeneous RF magnetic heating within the sphere, and also allows a rotational movement of chain-of-spheres assembly to induce mechanical-stirring based drug release as illustrated in FIG. 2(b) and FIG. 4.

These exemplary multiple trapped magnetic nanoparticles are fabricated by combination of various known approaches. For example, a synthesis of polystyrene spheres containing magnetic nanoparticles is followed by attachment of mercapto functional group using e.g. (3-mercaptopropyl)trimethoxysilane on the hydroxyl group of the polymer surface and attachment of a pre-made approximately 10 nm Au nanoparticle layer, followed by additional Au nanoparticle deposition by chemical reactions. In one embodiment, the gold- (Au—) shell coated polymer spheres are then treated with tetrahydrofuran ($(CH_2)_4O$, THF) or other polymer solvents such as hexane or toluene with mechanical stiffing to dissolve away the polymer so that only the magnetic particles remain within the hollow Au spheres, which are then washed/cleaned with acetone and ethanol or by heating to above the boiling point of THF, 66° C. A compound (e.g., a tracer, a drug) is then inserted into the hollow sphere.

For example, in the exemplary multiple magnetic nanoparticle of the invention, as illustrated in FIG. 7: the first image illustrates a plurality of magnetic nanoparticles within a 50 to 200 nanometer (nm) diameter (dia) polymer with 10 to 20 nm $Fe_3O_4$ particles, which is coated with a stacked layer of 5 nm Au particles; in the second image a 20 to 30 nm Au particle layer is illustrated, and the polymer is then etched away with e.g., tetrahydrofuran; the third image illustrates a plurality of approximately 20 nm $Fe_3O_4$ particles, and the fourth image illustrates that the hollow-shelled particles are then filled with a compound, e.g., a drug solution.

In alternative embodiments, either a single magnetic particle or multiple particles are provided within the sphere. The particle size and the Au coating thickness can be selected and controlled by experimentally determined processing specifics. In general, the cellular uptake of gold nanoparticles is strongly dependent on the gold particle size with approximately 50 nm diameter particles showing the maximum uptake, so the desired Au-coated drug delivery vehicle of this invention is desirably in the size regime of 20 to 200 nm in average diameter.

Figure 8:
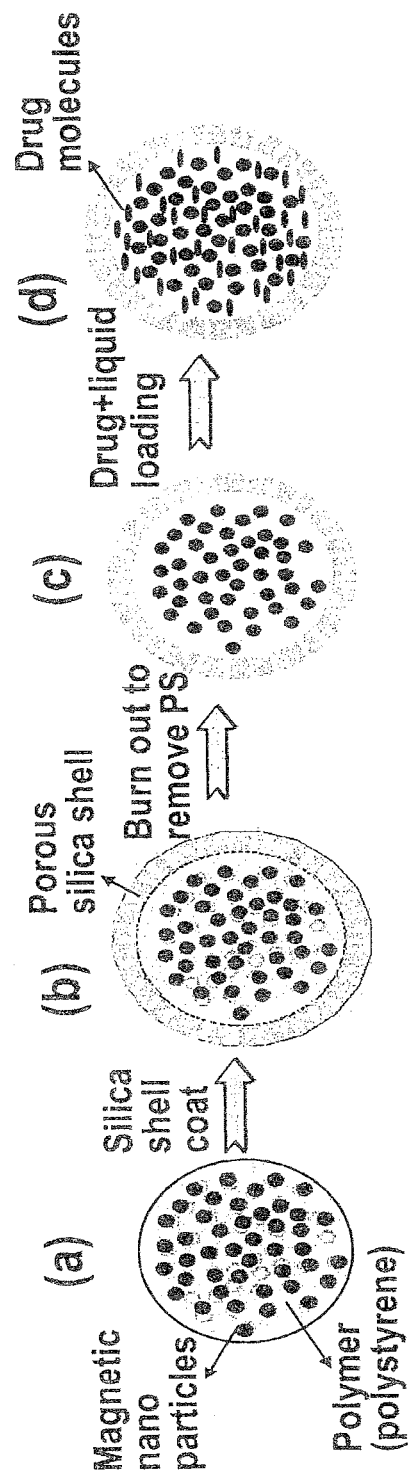
FIG. 8(a) illustrates magnetic nanoparticles of the invention comprising polymer aggregates of about 100-200 nm diameter, an example polymer being polystyrene, comprising a plurality of magnetic nanoparticles, which are then coated with a silica composition, which in one embodiment is made porous, as illustrated in FIG. 8(b), which this then burned out to make a porous shell.
as illustrated in FIG. 8(c), which this then loaded with a composition to be delivered, e.g., a drug or tracer, e.g., in liquid form as illustrated in FIG. 8(d), as discussed in detail, below.

Alternative embodiments of the invention utilize the hollow silica shell ($SiO_2$) configuration but introduce many (a plurality of) magnetic nanoparticles together with the intended compositions (e.g., tracers, drug(s) or biological agent(s)) to be released, as illustrated in FIG. 8. In alternative embodiments, this can be important because of the tremendously enhanced volume of magnetic nanoparticles with hundreds or thousands of particles closely assembled, which makes the heating or mechanical-stirring induced drug release much easier. In alternative embodiments, the enhanced magnetic moment can make magnetic gradient-field-induced movement of the drug containing capsule of this invention much easier and efficient as compared to a single or just a few magnetic particles.

Alternative embodiments of the invention are designed to overcome the blood-brain-barrier (BBB) so as to enable a delivery and release of CNS (central nervous system) drugs to the intended target in the brain. This embodiment allows both the delivery of the capsule across the BBB barrier and once it happens, a commanded, on-off release of the CNS drug.

In one embodiment, the first step to produce a structure as illustrated in FIG. 8; e.g., to form polymer aggregates of about 100 to 200 nm diameter (an example polymer being polystyrene) containing (comprising) many magnetic nanoparticles (e.g., at least 10, or at least 100, or at least 1000 particles of e.g., between about 10-30 nm diameter $Fe_2O_3$ or $Fe_3O_4$ (or other oxide or metallic alloy magnetic nanoparticles) as illustrated in FIG. 8(a). In one embodiment, the Fe oxide (magnetite or maghemite) nanoparticles are easily fabricated using well known chemical precipitation processes, for example, reacting a ($FeCl_3+FeCl_2$) mixed solution with ammonia $NH_4OH$ to precipitate out the about 10 to 30 nm, or 5 to 50 nm in diameter, regime magnetic particles.

In one embodiment, magnetite emulsion and styrene emulsion are prepared and mixed in a three-neck flask and stirred for 30 min at 200 rpm in nitrogen atmosphere. A microporous glass membrane (SPG™ membrane, SPG Technology Co., Ltd) is used as a base template to prepare styrene miniemulsion. In one embodiment, the reactor is placed in 80° C. water bath for 20 h to obtain $Fe_3O_4$/PS nanospheres suspension. Subsequently, the $Fe_3O_4$/PS nanospheres in the solution can be magnetically captured and collected by the magnet, are redispersed into 10 ml 0.5 wt. % polyoxyethylene sorbitan monolaurate aqueous solution with ultrasonic treatment to form a new suspension. In one embodiment, the suspension is added into 20 ml 2-propanol, under mechanical stiffing for 10 min. 0.5 ml ammonium hydroxide and various amounts TEOS are consecutively added into the above reaction solution, the amounts of TEOS are 36 µl, 210 µl, 880 µl corresponding to the silica shell thickness of approximately 2 nm, 10 nm and 30 nm, respectively. The silica encapsulation reaction can be performed at room temperature for 48 hours (h). The resultant silica-coated magnetic nanospheres are collected by a permanent magnet and washed three times by ethanol and water, respectively.

Figure 9:
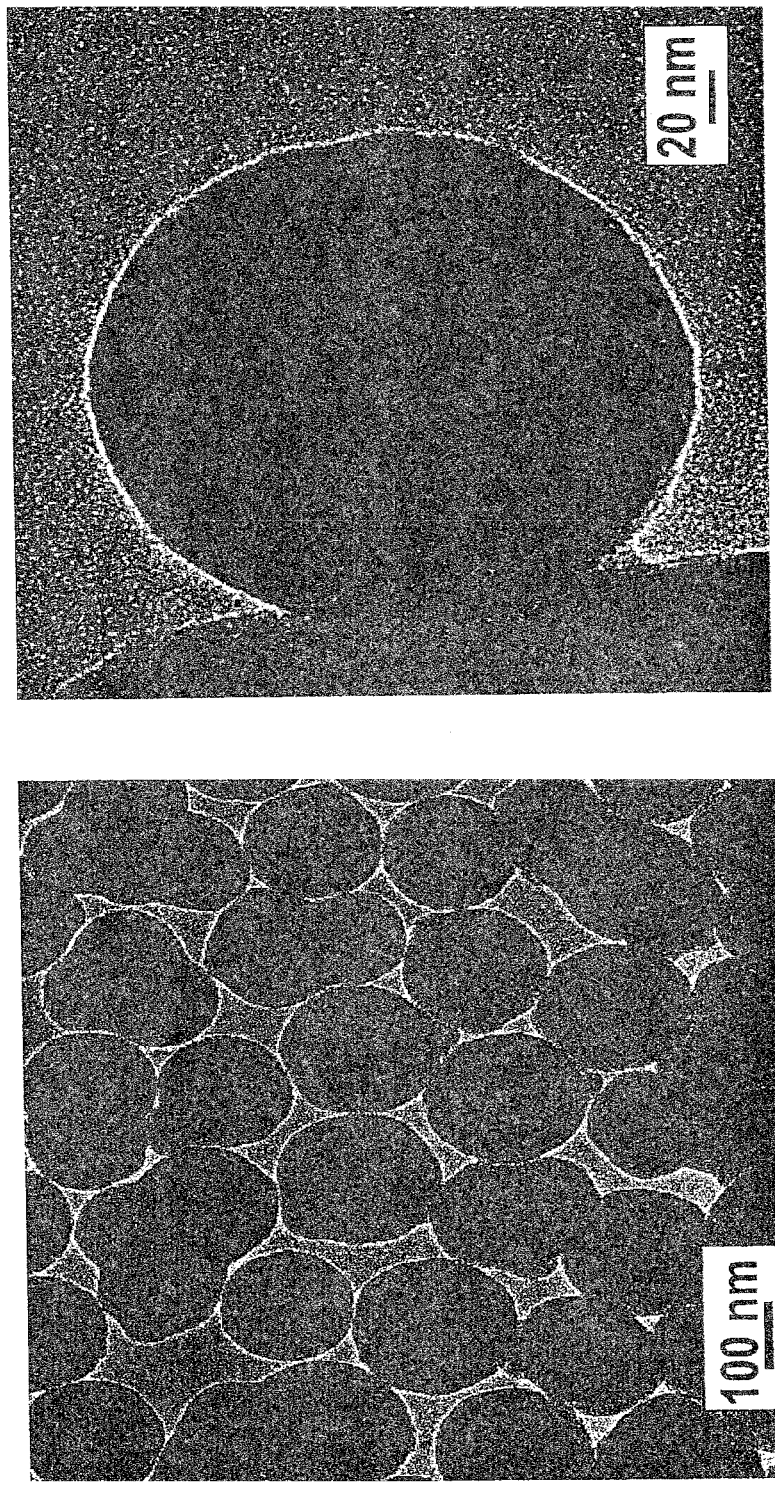
FIG. 9 illustrates a TEM micrograph showing an exemplary silica-coated polystyrene sphere with trapped magnetic nanoparticles, where

Shown in FIG. 9 is a TEM micrograph showing such exemplary composite particles with approximately 150 to 200 nm diameter, and a silica shell thickness of approximately 20 to 50 nm, and with several hundred magnetic nanoparticles trapped within the sphere. These exemplary silica coated composite particles, as illustrated in FIG. 8(b) and FIG. 9, are then heated ("burned out", as noted in FIG. 8(b)) to 300 to 500° C. for about 1 to 10 hrs in air to burn out the polystyrene inside the silica shell, which leaves only the inorganic magnetic nanoparticles within the shell, as illustrated in FIG. 8(c). In summary, FIG. 9 illustrates a TEM micrograph showing an exemplary silica-coated polystyrene sphere with trapped magnetic nanoparticles, where FIG. 9(a) illustrates a low magnified image, and FIG. 9(b) a high magnified image.

For example, in one embodiment, an anticancer drug, doxorubicin (e.g., ADRIAMYCIN™), was loaded by a vacuum drug loading method of placing the hollow spheres of FIG. 8(c) in a mechanical pump vacuum chamber, and letting the liquid containing the cancer drug into the chamber, and hence into the inside pores of the hollow silica vehicle. After the drug was loaded, the spherical carrier vehicle particles were repeatedly washed thoroughly by de-ionized water and centrifuged, and the supernatant was removed completely.

Figure 10:
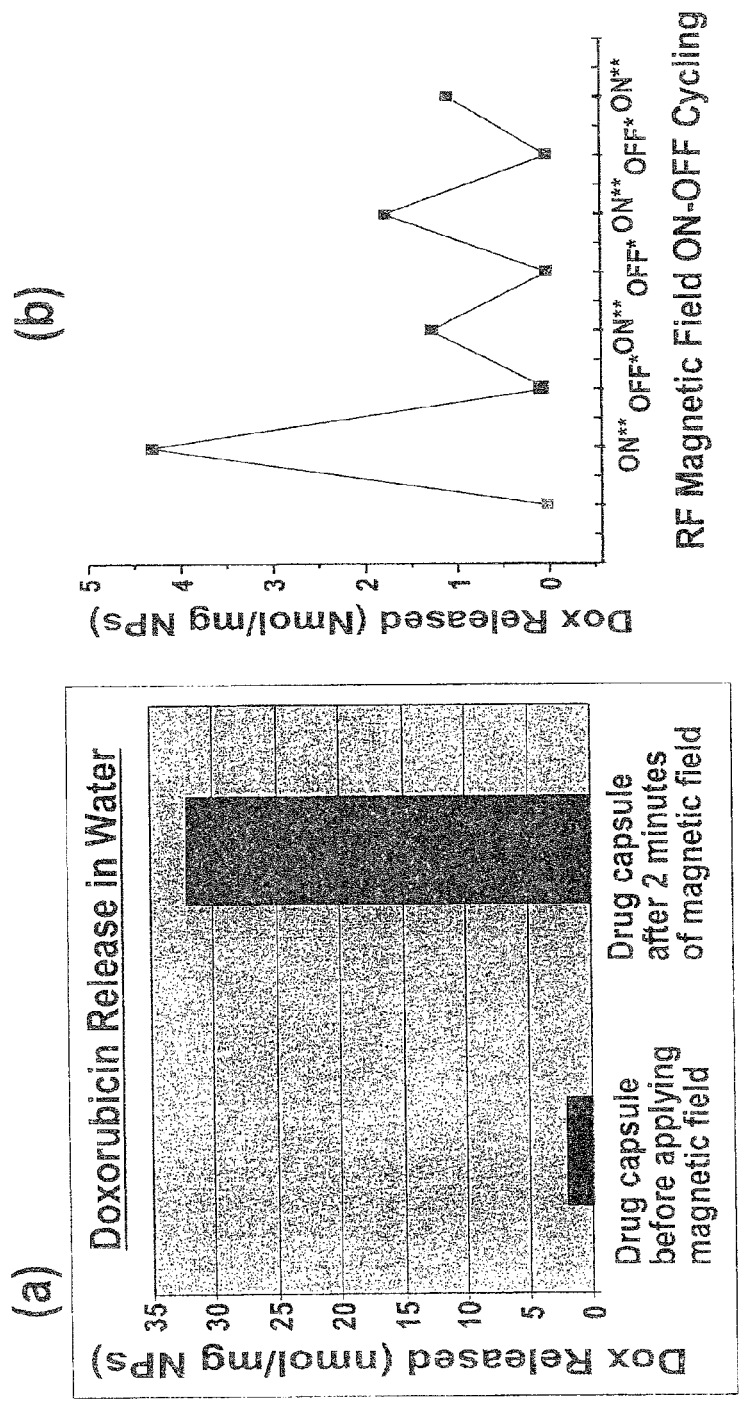
FIG. 10 graphically illustrates magnetic-field-induced drug release from these exemplary hollow silica capsules containing multiple magnetic nanoparticles and doxorubicin.

FIG. 10 graphically illustrates magnetic-field-induced drug release from these exemplary hollow silica capsules containing multiple magnetic nanoparticles and doxorubicin: FIG. 10(a) graphically illustrates data demonstrating enhanced drug release in water by 100 KHz magnetic RF field for 2 minutes; FIG. 10(b) graphically illustrates data demonstrating cyclic on-off switched drug release by magnetic field control.

The drug release characteristics of these exemplary hollow silica capsules of the invention, which contain (comprise) multiple magnetic nanoparticles loaded with doxorubicin drug (as with the FIG. 8(d)-type nanoparticles prepared as described above) was evaluated by subjecting the capsules suspended in water solution to an applied magnetic field (an approximately 100 KHz frequency RF field). The amount of drug release was measured by standard UV/visible spectrophotometer. When an external RF magnetic field is applied for 2 minutes, the drug release rate is significantly enhanced as shown in FIG. 10(a), by more than an order of magnitude larger than in the case of the capsule without applied field.

The capsules were also subjected to a cyclic magnetic field; as shown in FIG. 10(b). After each step of a 10 second exposure to magnetic field, the capsules were settled down to the bottom of the container by bringing close a permanent magnet for 2 min. After the solution became clear, the drug amount was measured using UV/visible absorption compared to the standard absorption characteristics for the drug. This 10 second exposure process is equivalent to the switch "ON" state for drug release. The capsules were then suspended again by stiffing, and the solution was left for 5 min without RF. When SiMNPs were settled down by magnet, the drug release amount in the absence of magnetic field was also measured by UV/vis spectrophotometer. This process is equivalent to the switch "OFF" state. The switch "ON-OFF" measurements were taken alternately for several cycles. As is evident from the data illustrated in FIG. 10(b) (the "Dox-released" Nmol/mg NPs of the y-axis) the drug release can be controllable ON and OFF at will by turning on or turning off the applied magnetic field; note the highest level of release was over 4 Nmol/mg. For chemotherapy or antibiotics therapy, such an on-off switching control is convenient and efficient for treatment as the drug is released according to the needed drug dose and interval, as well as adapting to the human body cycle needs, with minimal side effects.

While the invention is not limited by any particular mechanism of action, the observed switchable compound (e.g., tracer, drug) release from the magnetic particle-containing capsules is most likely a result of local heating, although the magnetic stiffing and mechanical vibration may also contribute. In one application, a remote magnetic RF field, due to the very high frequency involved, may not cause much movement of magnetic nanoparticles, but will simply induce heating of the particles due to energy absorption. Thus, in some embodiments, low frequency, direction-changing field cycles, or ultrasonic waves are used (e.g., are applied to the body) because magnetic stiffing and mechanical vibration occurs more readily with low frequency, direction-changing field cycles, or ultrasonic waves.

To demonstrate that the magnetic nanoparticles can be heated upon applied RF field, the following experiments were constructed.

Figure 11:
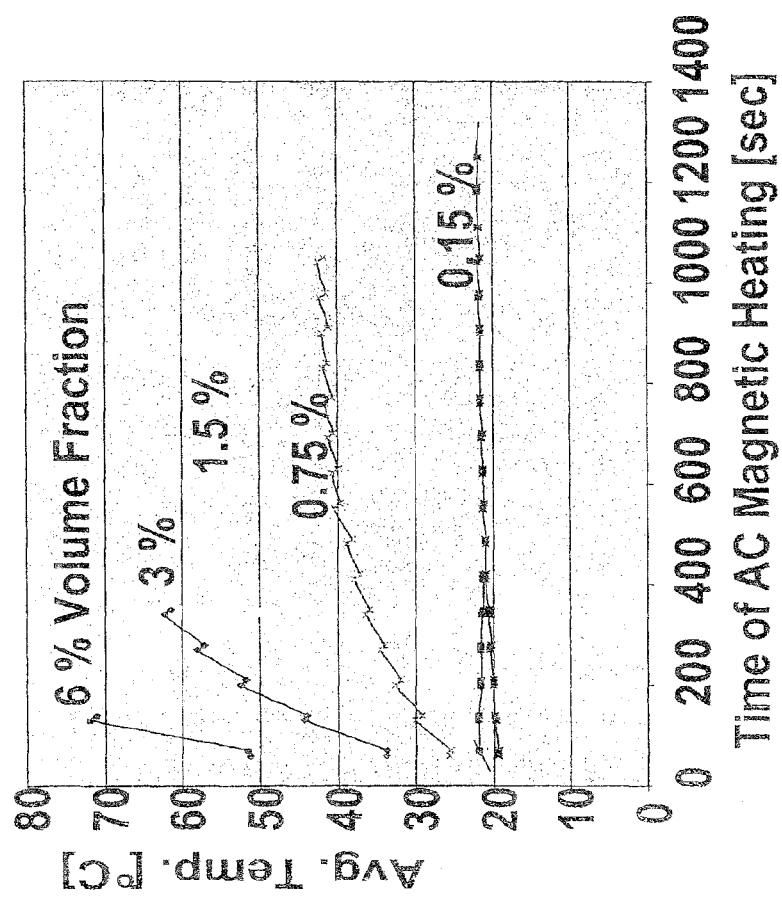
FIG. 11 graphically illustrates the average temperature rise in ° C. induced by a remote magnetic field in a liquid containing various amounts of exemplary magnetic nanoparticles of $Fe_3O_4$ as a function of the time of AC magnetic heating in sec, as discussed in detail, below.

Various concentrations of magnetic nanoparticles (of approximately 10 nm average diameter) in water were subjected to 100 KHz RF magnetic field and the temperature rise of the particle-containing solution was measured by optical fiber temperature sensor (to avoid RF heating of the sensor). The results are graphically illustrated in FIG. 11. The graph shows a time-dependent gradual temperature rise, capable of heating to at least 40 to 70° C. In alternative embodiments, if the hollow capsules containing magnetic nanoparticles such as $Fe_3O_4$ such particles and stored cancer drugs are heated to approximately 45° C. or higher, magnetic hyperthermia cancer treatment can be combined with drug-release based chemotherapy, thus providing further enhanced therapeutic functionality. The temperature rise inside the hollow sphere causes a temperature gradient inside versus (vs) outside of the sphere inducing diffusional delivery of the stored drugs from the sphere. In summary, FIG. 11 graphically illustrates the average temperature rise in ° C. induced by a remote magnetic field in a liquid containing various amounts of exemplary 10 nm magnetic nanoparticles of $Fe_3O_4$ (at 6%, 3%, 1.5%, 0.75%, and 0.15% volume fraction) as a function of the time of AC magnetic heating in seconds (sec); and the figure notes the 45° C. target for some exemplary magnetic hyperthermia treatments.

Biodegradable Polymer Shell Hollow Spheres with Trapped Magnetic Particle(s)

Figure 12:
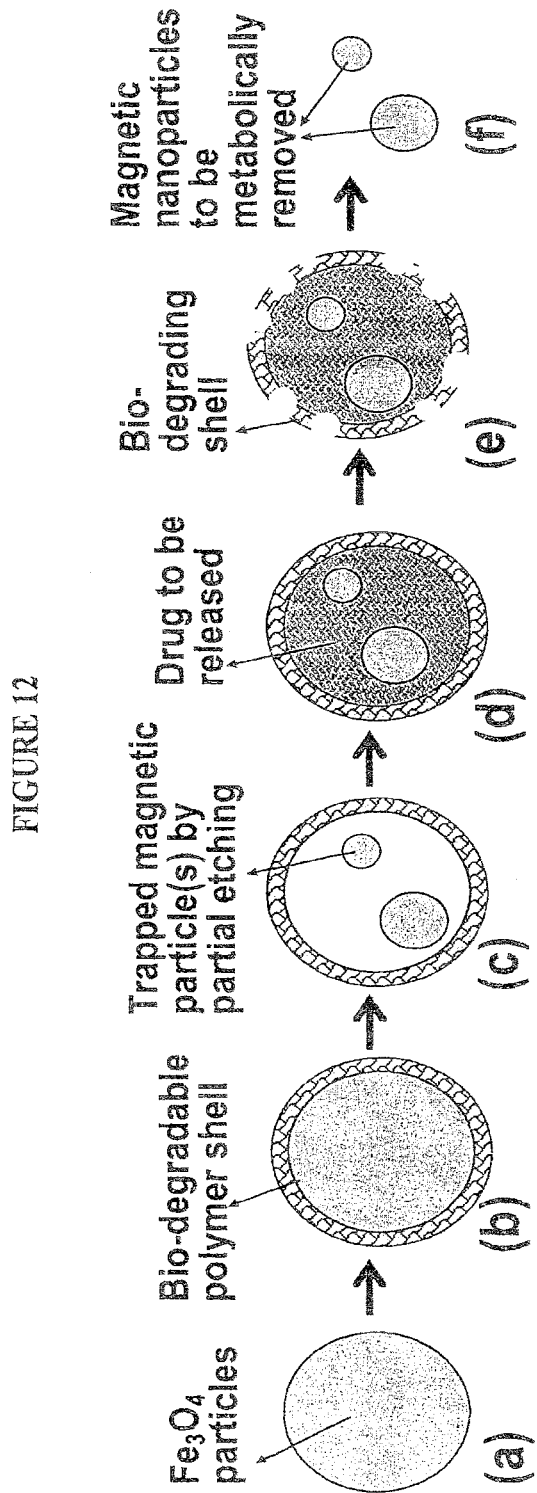
FIG. 12(a) illustrates an exemplary $Fe_3O_4$ nanoparticle of the invention, which in FIG. 12(b) is illustrated to comprise a biodegradable shell, which in FIG. 12(c) is illustrated to comprise magnetic particles contained ("trapped") therein by partial etching; which in FIG. 12(d) is illustrated to comprise a composition (e.g., tracer, drug or the like) contained ("trapped") therein; which in FIG. 12(e) is illustrated to have a biodegraded shell; and in FIG. 12(f) the magnetic nanoparticles within the $Fe_3O_4$ nanoparticle of the invention are metabolically removed, as discussed in detail, below.

Another exemplary embodiment of the invention comprises a hollow capsule magnetic composition—(e.g., tracer-, drug-) delivery system utilizing a bio-degradable and/or bio-resorbable material as the hollow shell material to trap the magnetic nanoparticles. For example, alternative embodiments of this hollow composition—(e.g., tracer-, drug-) delivery composition of the invention comprises any known bio-degradable and/or bio-resorbable material as the hollow shell material to trap the magnetic nanoparticles, as illustrated in FIG. 12. These bio-degradable materials can be coated using the well known polymer coating techniques on the surface of magnetic nanoparticles, and the interior magnetic materials can be partially dissolved away using dilute acid, as illustrated in FIG. 3. FIG. 12(a) illustrates an exemplary $Fe_3O_4$ nanoparticle of the invention, which in FIG. 12(b) is illustrated to comprise a biodegradable shell, which in FIG. 12(c) is illustrated to comprise magnetic particles contained ("trapped") therein by partial etching; which in FIG. 12(d) is illustrated to comprise a composition (e.g., tracer, drug or the like) contained ("trapped") therein; which in FIG. 12(e) is illustrated to have a biodegraded shell, i.e., the shell is biodegraded in vivo/in situ; and in FIG. 12(f) the magnetic nanoparticles within the $Fe_3O_4$ nanoparticle of the invention are metabolically removed, i.e. removed and cleared by the body (cleared in vivo/in situ).

Figure 13:
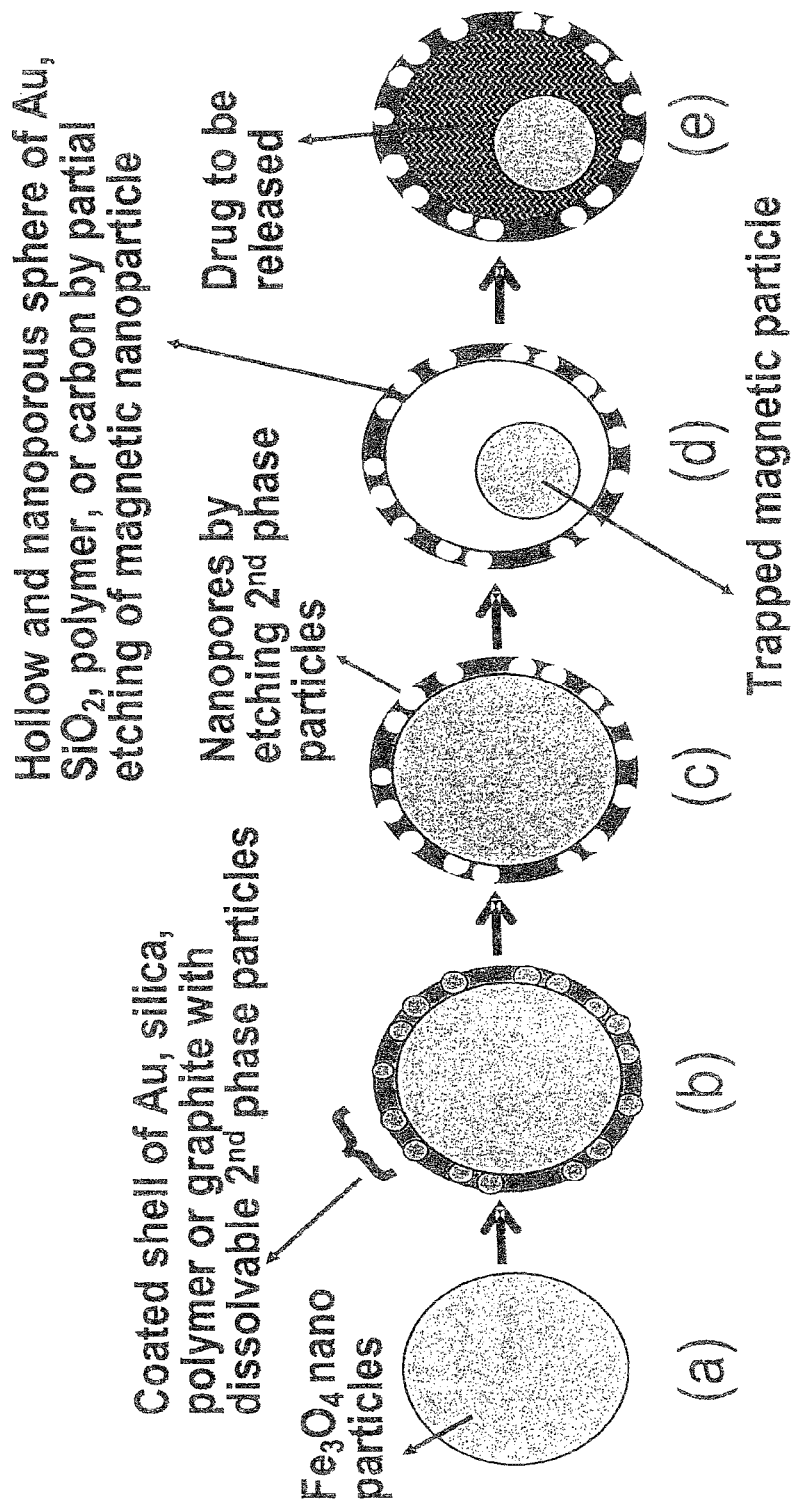
FIG. 13(a) illustrates an exemplary $Fe_3O_4$ nanoparticle of the invention; which in FIG. 13(b) is illustrated to comprise a coated shell of gold (Au), silica, polymers of graphite, and the like, comprising dissolvable "second phase" particles; where
FIG. 13(c) illustrates the creation of nanopores by the etching of the second phase particles.
FIG. 13(d) illustrates inclusion, or "trapping", of magnetic particles (where hollow and nanoporous spheres of gold (Au), silica, polymers of graphite, and the like are created by etching)
FIG. 13(e) illustrates inclusion, or "trapping", of a composition, e.g., a drug to be released, as discussed in detail, below.

If needed, the porosity in the polymer shell can intentionally be increased, for example, by dissolving away pre-mixed metal or metal oxide nanoparticles within the bio-degradable layer as illustrated in FIG. 13 (see further discussion below regarding this embodiment). Well-known, bio-degradable materials such as polylactic-polyglycolic acid (PLGA) copolymers previously used for composite synthesis with magnetic particles, dextran grafted with poly (N-isopropylacrylamide-co-N,N-dimethylacrylamide) or elastomeric poly (phosphoester urethane) can be utilized as the shell material. In one embodiment, PLGA type biodegradable polymers, PEG modified PLGA, or surface modified PLGA with poly(L-lysine)-g-poly(ethylene glycol) (PLLg-PEG) known to prevent excessive binding of plasma proteins are used. In one embodiment, the surface of FIG. 12(d) nanosphere vehicles are made more resistant to protein binding if needed so that retention of the drug-releasing nanosphere in systemic circulation can be prolonged. In alternative embodiments, coating the nanoparticles with certain surface ligands or other functional groups that inhibit or block the protein binding is used and can be beneficial, especially if antigens that like to bind to tumor or tissue surfaces are well utilized.

When the drug is eventually consumed by controlled release operations, the shell material will gradually be biodegraded, as illustrated in FIG. 12(e), while the magnetic nanoparticles will be absorbed and metabolically discarded by human body, as illustrated in FIG. 12(f). Either a single magnetic particle based or multiple particle based biodegradable shells can be utilized.

Artificially Pored, Biodegradable Polymer Shell Structured Hollow Spheres with Trapped Magnetic Particle(s)

In one embodiment, the invention provides a nanoparticle with a two-phase-nanocomposite coating, e.g., as illustrated in FIG. 13. Compositions of the invention can be designed and manipulated to accommodate a desired release rate of a tracer, drug or biological agent from a hollow capsule with trapped magnetic particles; where the desired release rate depends on the specific nature of the disease or state of a patient's health, patient's age or weight, the state of the disease progress, and so forth. In some aspects of the invention, where there is a need to further accelerate the release rate from a hollow sphere capsule of the invention, an artificially induced pored shell structure is designed and utilized.

As illustrated in FIG. 13, the invention provides compositions comprising a two-phase-nanocomposite coating such as a metal-containing polymer or a copolymer; these can be utilized to artificially introduce a larger diameter, higher density nanopore on the shell material. In alternative embodiments, the needed porosity with a desired size in the shell are intentionally created, for example, by:

(i) first, coating the magnetic sphere surface with a bio-degradable polymer layer containing pre-mixed metal oxide nanoparticles, as illustrated in FIG. 13(b), of desired size, such as e.g. the oxide particles Ni, Cu, Co and/or Fe, which are easily fabricated by chemical precipitation methods of [$FeCl_2$+$FeCl_3$+$NH_4OH$] reaction. TEM images for exemplary fabricated 2, 6, 15 nm $Fe_3O_4$ magnetite nanoparticles of the invention shown in FIG. 14(a), FIG. 14(b), and FIG. 14(c), respectively.

(ii) second, selectively dissolving away pre-mixed metal oxide nanoparticles (such as iron oxide nanoparticles within the shell of bio-degradable coating layer using a dilute acid, or selectively dissolving one of the two copolymer phases (e.g., polystyrene+PMMA (polymethyl methacrylate)) using a solvent to intentionally create more nanopores or larger sized nanopores. This is illustrated in FIG. 13(c).

In alternative embodiments, the average pore size in the hollow sphere shell is in the range of about 1 to 40 nm, or 2 to 20 nm, or 5 to 10 nm, in diameter. Once the nanopores are introduced, the interior magnetic particle(s) can be partially etched away to form porous shell spheres with a trapped magnetic nanoparticle, e.g., as in the exemplary embodiment as illustrated in FIG. 13(d). The drug to be administered is then inserted to the interior, see the exemplary embodiment as illustrated in FIG. 13(e), and as discussed earlier.

In summary, FIG. 13(a) illustrates an exemplary $Fe_3O_4$ nanoparticle of the invention; which in FIG. 13(b) is illustrated to comprise a coated shell of gold (Au), silica, polymers of graphite, and the like, comprising dissolvable "second phase" particles; where FIG. 13(c) illustrates the creation of nanopores by the etching of the second phase particles; and FIG. 13(d) illustrates inclusion, or "trapping", of magnetic particles (where hollow and nanoporous spheres of gold (Au), silica, polymers of graphite, and the like are created by etching); and FIG. 13(e) illustrates inclusion, or "trapping", of a composition, e.g., a drug to be released.

In alternative embodiments, selection (construction) of the smaller pores (e.g., about 1, 2, 3, 4, 5, 6 or more nm diameter) in the shell is favored for storage of a composition, e.g., a hydrophilic drug or tracer, which could easily move in and out of the nanometer sized shell wall pores. An exemplary hydrophilic drug is doxorubicin; an exemplary tracer is an MRI and/or a positron emission tomography (PET) imaging compound such as a 18-fluorodeoxyglucose, e.g., a [18F]-2-fluoro-2-deoxyglucose, 6-[$^{18}$F]-fluoro-L-dopa (FDOPA), or a [18F]-3'-fluoro-3'-deoxythymidine. In alternative embodiments, larger pores may be preferred, e.g., for a hydrophobic drug such as docetaxel.

Figure 14:
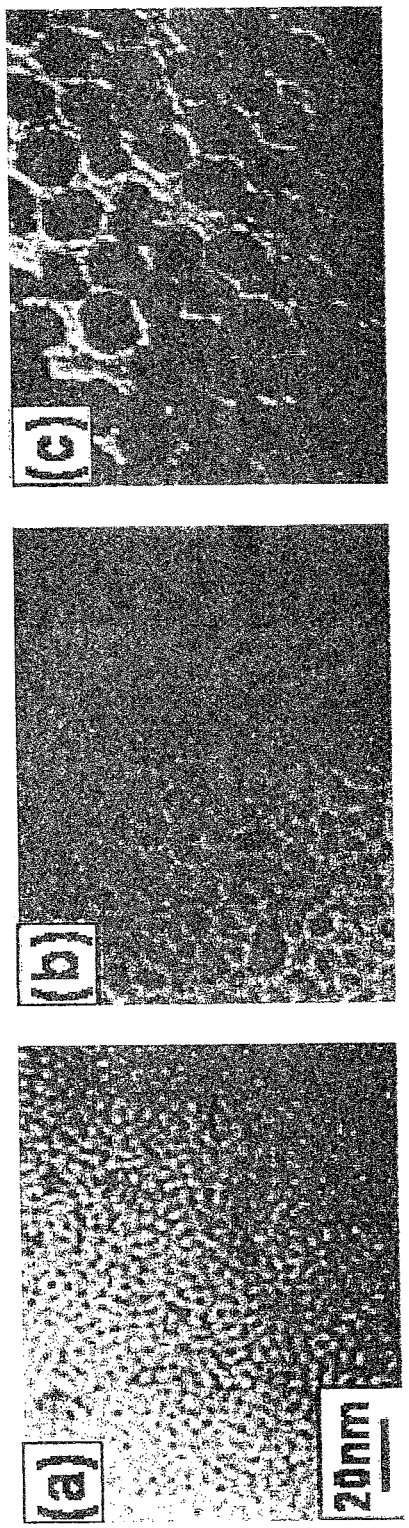

FIG. 14 illustrates images of exemplary $Fe_3O_4$ nanoparticles with: FIG. 14(a) 2 nm, FIG. 14(b) 6 nm, FIG. 14(c) 15 nm diameter pores. If in an alternative embodiment a shell pore size control toward smaller pores is desired, e.g., to obtain a slower kinetics of drug release over extended period of time, an optional high temperature annealing treatment (e.g., 500° C. to 900° C./1 hr) can be utilized to partially fuse and consolidate the layer of coated silica nanoparticles or Au nanoparticles and reduce the pore size.

In alternative embodiments, a method of artificially introducing nanopores into the polymer shell structure can be utilized for inorganic shell materials such as silica, gold or other ceramic and metallic shell hollow materials, such as those nanoparticle embodiments illustrated in FIGS. 1 through 9.

As mentioned in reference to embodiments illustrated in FIG. 2(a), alternative embodiments of the invention comprise compositions and methods for composition (e.g., a tracer or drug) release from a switchable capsule vehicle containing (comprising) magnetic particles, wherein the release can be activated by using remotely applied ultrasonic waves and/or an RF magnetic field. While the invention is not limited by any particular mechanism of action, mechanical motion and/or vibration of the magnetic particles are the main mechanism of drug release. In one embodiment, since the ultrasound waves will also vibrate the capsules themselves, the composition (e.g., a tracer or drug) release is further re-enhanced by the ultrasound. In alternative embodiments, desired frequencies of such ultrasonic waves can be in the range of about 20 KHz to 10 MHz, or in the range of about 200 KHz to 2 MHz.

Magnetic Targeting and Drug Release Using Hollow Capsule Vehicles

In alternative embodiments, the invention provides compositions (e.g., the nanoparticles of the invention) comprising targeting molecules, e.g., molecules that can specifically target a particular cell, tissue or organ phenotype, whether that phenotype be normal or abnormal, e.g., a targeting molecule that targets only cancer cells, or targets only a specific type of cancer cell.

In alternative embodiments, for efficient compound (e.g., biologic, drug or tracer) release applications, targeting for specific tumor cells is used. Targeting molecules such as antibodies, e.g., an antibody that can specifically bind to, or "target", a cancer cell, e.g., such as an IgG, or immunoglobulin G, can be attached onto the surface of a particle of the invention, e.g., a drug capsules as illustrated in FIGS. 1 to 9, 12, 13, and 15.

In alternative embodiments, compounds, e.g., proteins or polysaccharides, that assist in the process of nanocapsules uptake into a cell (e.g., the cell's cytoplasm) are added onto the surface of a composition (e.g., the nanoparticle) of the invention, e.g., a drug capsule of the invention, e.g., in order to enhance receptor-mediated endocytosis. Example of such compounds, e.g., proteins or polysaccharides, include any ligand specific for a receptor (e.g., a cytokine receptor, a transferrin receptor, etc) on a targeted cell, or a knock-out serum albumin (KSA), and the like.

In alternative embodiments nanoparticles of the invention (e.g., the drug delivery capsule vehicles of the invention) have a strong magnetic strength due to the assembly of many magnetic particles; in contrast to other embodiment that comprise individual, approximately 10 nm magnetic particles. In alternative embodiments nanoparticles of the invention comprise superparamagnetic nanoparticles of e.g. $Fe_2O_3$ or $Fe_3O_4$. In alternative embodiments, when there are more than 10 nanoparticles or more than a few hundred nanoparticles closely aggregated, the magnetic interaction force applied can be much more powerful than when using embodiments having only a single or a few superparamagnetic particles; in some applications the magnetic interaction force applied can be much more powerful by orders of magnitude depending on the total number of closely spaced magnetic particles in the capsule.

Therefore, in alternative embodiments magnetically or ultrasonically remote switchable delivery compositions of the invention (e.g., drug delivery capsules) comprising comprise superparamagnetic nanoparticles also can be used for targeting vector movements of the compositions (e.g., drug capsules) to confirm and ascertain desired locations or cells, tissues, and/or organs for targeting in an individual, e.g., in a human or an animal's body. Two exemplary uses of the switchable compositions (e.g., drug delivery capsules) of the invention comprise:

(1) Gradient magnetic field guidance of the capsules to specific desired neural cell regions in the brain by enable to cross the BBB (Blood-Brain-Barrier) followed by switchable drug release using RF magnetic field or ultrasound activation; and (2) External magnet induced, position-fixed accumulation of capsules for preferential drug delivery to certain desirable locations (e.g., to specific cells, tissues, and/or organs) followed by switchable composition (e.g., tracer, drug) release using RF magnetic field or ultrasound activation.

In alternative embodiments, methods of the invention comprise use of such gradient magnetic field guidance and/or external magnet induced, position-fixed guidance of magnetic nanoparticles for delivery of particles to the central nervous system (CNS), including the brain and the spinal cord. In alternative embodiments, compositions and/or methods of the invention are used to diagnose, treat and/or ameliorate individuals who suffer from a CNS disease such as Alzheimer's disease, schizophrenia, epilepsy, multiple sclerosis, stroke and brain tumors, and including any cardiovascular disease pertaining to the heart and/or blood vessels.

In alternative embodiments, compositions and/or methods of the invention are designed to cross into the "Blood Brain Barrier (BBB)" and cross over the BBB's endothelial cells that tightly overlap each other at "tight junctions". In alternative embodiments, compositions and/or methods of the invention are designed to deliver of a large number of tracers and/or drugs, including central nervous system (CNS)-active tracers (e.g., PET or MRI imaging agents), drugs, antibiotics, antineoplastic agents, and therapeutic drugs to the CNS, e.g., to brain tumors.

In alternative embodiments, compositions and/or methods of the invention target CNS (e.g., brain) capillary endothelium to enhance the penetration of nanoparticles of the invention, with their payload of compositions, e.g., tracers and/or drugs, into the CNS, e.g., brain tissue. For example, in alternative embodiments composition-loaded (e.g., tracer- or drug-loaded) nano-carriers of the invention capable of recognizing brain capillary endothelial cells and/or cerebral tumoral cells use site-specific ligands for targeting, e.g., for use in oncology. In alternative embodiments, endogenous and/or chimeric ligands that can bind to carriers or receptors of the BBB, directly or indirectly, are conjugated or otherwise attached to nanocarriers of this invention.

In alternative embodiments, compositions and/or methods of the invention transport compositions (e.g., tracers and/or drugs, including CNS-active tracers (e.g., PET or MRI imaging agents), drugs, antibiotics, antineoplastic agents, and therapeutic drugs) across the BBB by:

(i) direct injection into intended site for drug delivery. This injection process can be used in humans, and can be highly efficient for drug delivery; but it may involve invasive procedures and may requires specialist medical teams and equipment;

(ii) permeation through tight junctions using osmotic disruption or biochemical opening, which leads to a reversible but non-specific opening of the tight junction to allow drug transport across BBB;

(iii) enhanced drug delivery through the endothelial cells (transcytosis) to the underlying brain cells by utilizing the endocytosis mechanism using liposomes or nanoparticles loaded with the drug to be delivered. This exemplary approach can be further enhanced by receptor mediated endocytosis specifically targeting the delivery system to receptors on the brain endothelium surface; and/or (iv) use of nanoparticles of the invention to enhance drug delivery across BBB. The small size of nanoparticles of the invention having functionalizable surfaces can be an advantage as drug delivery carrier.

Figure 15:
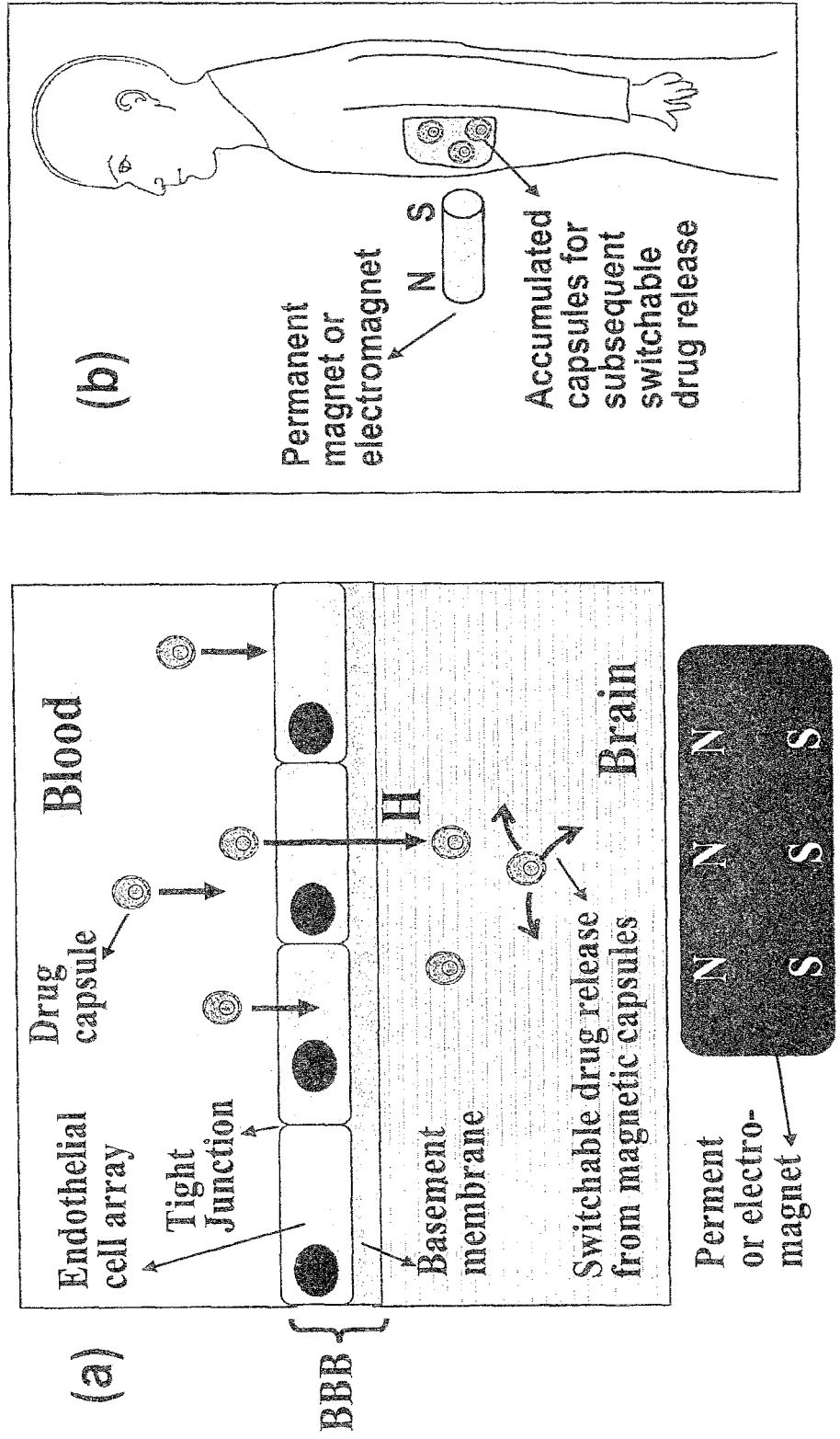
FIG. 15 illustrates exemplary guided composition (e.g., tracer, drug) delivery using magnetically switchable nanoparticles of the invention (e.g., drug capsules)

In alternative embodiments, compositions and/or methods of the invention comprise use of guided composition (e.g., tracer, drug) delivery using magnetically switchable nanoparticles of the invention (including e.g., drug capsules), e.g., as schematically illustrated in FIG. 15.

FIG. 15(a) illustrates the embodiment comprising application of a DC magnetic gradient field (e.g., using a magnet with the surface field strength of at least about 100 Oe, or at least about 1,000 Oe, or at least about 3,000 Oe) to induce the magnetic nanoparticle assembly within the capsule to respond and move toward the direction of the gradient magnetic field. This allows extra driving force for the nanoparticles of the invention (e.g., drug capsules) to cross the BBB and reach the cells in certain desired CNS regions, e.g., brain cells, as illustrated in FIG. 15(a).

Once the BBB is crossed, the nanoparticles of the invention (e.g., drug capsules) can be activated (switched-on) by remote RF magnetic field and/or ultrasonic activation for composition (e.g., tracer, drug) release.

In alternative embodiments, in practicing the compounds and methods of this invention, the crossing of proteins, particles, tracers, drugs, etc. through the BBB can occur via a variety of mechanisms such as increased pinocytosis and transcytosis (both forms of endocytosis), the formation of transendothelial channels, opening of the intercellular tight junctions and disruption of endothelial cell membrane integrity. The use of a magnetic capsule can help these processes for enhanced BBB crossing.

In alternative embodiments, an assembly of magnetic nanoparticles is used rather than isolated particles; in some applications this can be essential to provide strong magnetic interaction force and to cross the BBB. In one aspect, a desired magnetic particle configuration for BBB crossing is that each capsule contains (comprises) between about 10 and 1000 particles, or between about 10 and 500 particles, between about 10 and 100 particles, or at least 10 particles, or at least 100 particles; and in alternative embodiments, their average inter-particle spacing is less than 100 nm, or is less than 50 nm, or is less than 20 nm, or is less than 10 nm. In alternative embodiments, isolated magnetic nanoparticles with a diameter in the regime of between about 5 to 20 nm are used; they tend to be superparamagnetic, with orders of magnitude weaker magnetic interaction force than ferromagnetic particles.

In alternative embodiments, in addition to the magnetic pulling force, another technique that can be employed comprises locally heating the nanoparticle of the invention (e.g., a drug capsule) using a magnetic RF field (similarly to that used in magnetic hyperthermia heating) to introduce local thermal stress to disrupt the BBB barrier for easier crossing; general temperature rise of the neural cells is known to enhance BBB crossing.

In alternative embodiments, magnetic capsules can enhance the positioning of compound (e.g., drug, tracer) release. For example, the strong magnetic interaction of the many particles in a nanoparticle (e.g., a drug capsule) of the invention can be utilized for local accumulation of the nanoparticles, for example, the nanosized particle (nanoparticles) of the invention (e.g., drug capsules) circulating in the blood vessel can be guided to accumulate near a position of the pre-positioned permanent magnet or electromagnet, as illustrated in FIG. 15(b). The drug capsules are then activated (switched-on) by remote RF magnetic field or ultrasonic activation for drug release. Optionally, a slow dragging movement of the magnet(s) can be utilized to relocate the accumulated drug capsules to neighboring organ regions.

FIG. 15 illustrates exemplary guided composition (e.g., tracer, drug) delivery using magnetically switchable nanoparticles of the invention (e.g., drug capsules): FIG. 15(a) illustrates the BBB crossing of nanoparticles of the invention using magnetic gradient field and subsequent composition (e.g., tracer, drug) release by remote RF field and/or ultrasonic activation in the intended brain location, FIG. 15(b) illustrates magnetic position fixing of accumulation of nanoparticles of the invention (e.g., drug capsules) and subsequent composition (e.g., tracer, drug) release by RF field or ultrasonic activation. A slow dragging movement of magnets to relocate the accumulated nanoparticles of the invention (e.g., drug capsules) is also possible.

Nano-Reservoir Array with Latchable Valves

The invention provides products of manufacture comprising nano-reservoir arrays with "latchable" valves. This embodiment can be used in any composition (e.g., tracer, drug) release application, e.g., for insulin release for diabetes, or tracer release for PET. In one embodiment, a position-fixed drug device, rather than mobile nanoparticles or nanocapsules is used, e.g., as illustrated in FIG. 16(a) and FIG. 16(b), which are schematic illustrations of exemplary magnetically switchable and "latchable" drug delivery vehicles of this invention based on this "nano-reservoir array" concept.

In one embodiment, nano-reservoir cavity arrays are fabricated by DUV (deep UV) lithography, e.g., as 8 inch wafers or by nano-imprint lithography. In one embodiment, an exemplary nano-reservoir cavity array of the invention has a dimension of approximately 160 nm dia×600 nm deep, or 320 nm dia×950 nm deep, e.g., as illustrated in FIG. 16(c). In one embodiment, an exemplary nano-reservoir cavity array of the invention has as small as 100 nm dia.; this dimension cavity array has been made. These cavity spaces can be utilized as a vehicle to store compounds to be release (e.g., tracers, drugs or biological agents), which can then be released only when a command is given by remote signaling to open the valve and release the compound.

Figure 16:
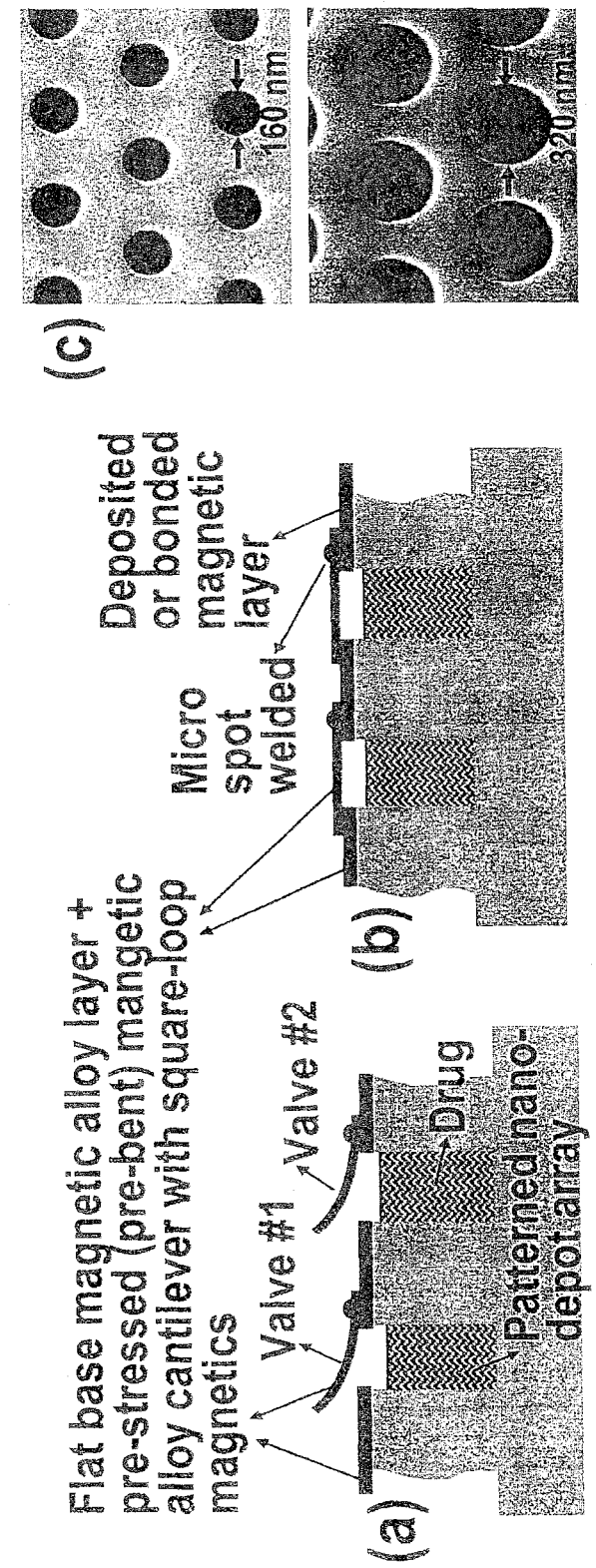
FIG. 16 illustrates an exemplary nano-reservoir array with latchable valves made of a stainless steel type magnetic alloy that is remotely triggerable with a pulse magnetic field.

FIG. 16 illustrates an exemplary nano-reservoir array with latchable valves made of a stainless steel type magnetic alloy that is remotely triggerable with a pulse magnetic field: FIG. 16(a) illustrates a patterned nano-depot array comprising a flat base magnetic alloy layer with a pre-stressed (e.g., pre-bent) magnetic alloy cantilever with square-loop magnetics, illustrating exemplary valve #1 and valve #2 releasing a composition (e.g., a tracer, a drug); the illustration shows a valve open with the magnetic base and the magnetic cantilever demagnetized; FIG. 16(b) illustrates the array of FIG. 16(a) but with the valves closed when the magnetic components are magnetized; FIG. 16(c) illustrates exemplary silicon (Si) nano-patterned cavity arrays having 160 nm and 320 nm diameter cavities.

In one embodiment, for on-off switchable composition (e.g., a tracer, a drug) delivery, the invention provides a magnetically responsive lid structure attached onto the entrance of the compounds (e.g., tracer, drug, biological agent) delivery vehicle. In one embodiment, the top lid of the exemplary nano-reservoir cavity (valve) is made of special, square M-H loop magnetic materials with easily switchable coercivity, as described e.g., in references 24, 25, 26 and 27, listed below.

In one embodiment, it is desirable that the alloy used for the lid is chemically inert, e.g., based on stainless-steel-based (e.g., Fe—33% Cr—9% Co or Fe—20% Cr—4% Ni wt %) and bio-compatible. In one embodiment, the alloy surface is coated with chemically inert or biocompatible film comprising gold (Au), platinum (Pt), palladium (Pd) and/or their alloys.

In alternative embodiments, the magnetic layer is either an approximately 10 to 100 µm thick, sputter deposited film layer or a lamination bonded thin sheet. In alternative embodiments, the magnetic layer is magnetic field annealed (e.g., as described in references 24 or 25, below) or deformation aged (e.g., as described in references 26 or 27, below) to induce in-plane square M-H loop characteristics with "latchability".

In one embodiment, the magnetic field is applied for just a fraction of a second (e.g., on the order of milliseconds) and then can be turned off, still retaining the intended magnetization state, as illustrated in FIG. 16(a), keeping the valve "closed" or "open" position without power use. FIG. 16(b) shows an example elongated magnetic nanostructure which imparts the square M-H loop and the "latchability". Such a latchability capability requiring only a split second magnetic field to activate (SWITCH—ON) and deactivate (SWITCH—OFF) the drug release vehicle can be an important aspect of this embodiment, as a continual application of magnetic field to release the drug may be cumbersome and inconvenient for some uses, e.g., for diagnostic or therapeutic applications.

In one embodiment, the flat base magnetic layer (onto which the switchable valve membrane, e.g., a cantilever, is magnetically attracted and contacted) is fabricated by thin film deposition onto the top surface of pre-patterned Si cavity array, or blanket thick film deposition, followed by nanopatterning using the known DUV (deep UV) photolithography etching, laser lithography or nano-imprint lithography. In one embodiment, the metal pattern itself is used as a mask (with an optional protective coating of inert metal or oxide) to pattern the underlying Si into cavity holes array, e.g., as illustrated in FIG. 16(c). Alternatively, an array of pre-patterned base magnetic layer can be separately fabricated on an alloy sheet (or foil), brought to the top surface of the Si cavity array for alignment, and transferred onto the Si base cavity array, and bonded by adhesives or array micro spot welding.

In one embodiment, another set of the same stainless steel, square loop magnetic sheet with a round, oval or rectangular cantilever array pre-patterned is then aligned and bonded onto the base magnetic alloy using either micro spot welding, laser welding, or diffusion bonding. Pre-stressing and bending of the alloy sheet prior to bonding is easily accomplished by cold rolling, and such a stressed sheet is flattened and bonded after which the cantilever is etch patterned to be partially released and bent up as in FIG. 16(a). Alternatively, the cantilevers can be made to bend up by simple sputter deposition of another metal layer such as Au or Cr on the top surface only (in analogy to the well known bi-metal principle). While stainless steel can be basically bio-compatible, the magnetic alloy may optionally be coated with other bio-inert materials such as gold (Au), Pt, Pd and/or their alloys, and/or PEG (polyethylene glycol).

The exemplary latchable valves in FIG. 16 can be opened or closed at will, using remotely applied pulse magnetic field. The balance of force involved here are the mechanical spring force of bent metal foil cantilever vs magnetic attraction force between the base magnet and the cantilever magnet. For a stronger magnetic valve attraction force, the base magnet force can be increased, if necessary, by thickness control and selection of magnetic materials, while the spring force can be reduced, if needed, by making the cantilever thinner.

Figure 17:
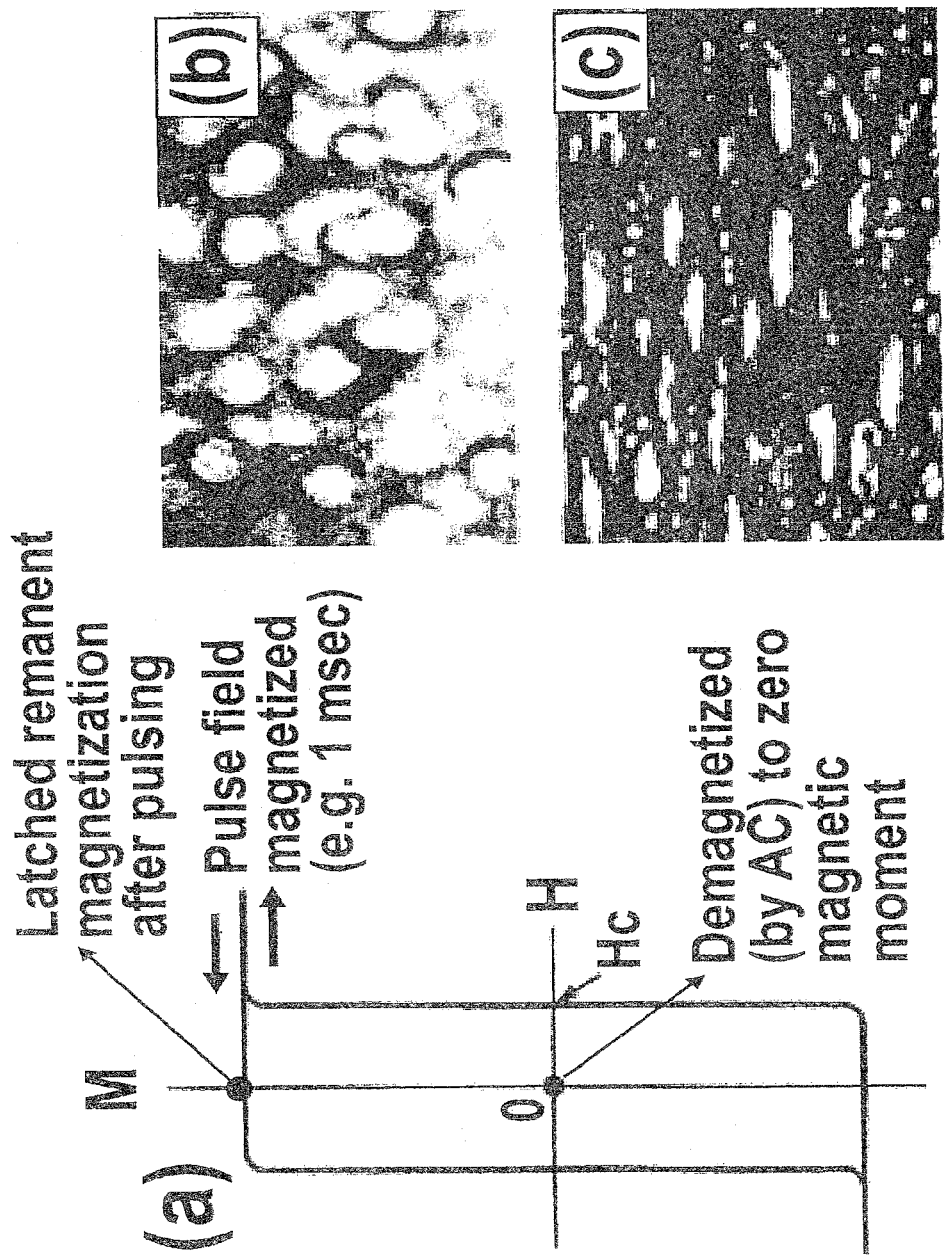
FIG. 17 illustrates an exemplary magnetically switchable and latchable valve with semi-hard, square-loop M-H loop characteristics.

In one embodiment, for switch operation a demagnetizing field (such as a commonly used gradually intensity-decreasing 60 Hz magnetic field) is used to reduce the remnant magnetization of both the base magnet and the cantilever magnet to zero, as graphically illustrated in FIG. 17(*a*), the point of origin, which allows the valve to open (pre-bent cantilever spring back to open the cavity, as in FIG. 16(*a*)) to start releasing the compound to be released (e.g., a tracer, drug and the like). In one embodiment, to close the valve, as illustrated in FIG. 16(*b*), to stop the compound (e.g., a tracer, drug and the like) from being delivered, a DC magnetizing field is remotely applied and removed so as to magnetize both the base magnet and the cantilever magnet to the latched remnant magnetization point (FIG. 17(*a*)) for magneto-static attraction.

FIG. 17 illustrates an exemplary magnetically switchable and latchable valve with semi-hard, square-loop M-H loop characteristics: FIG. 17(*a*) graphically illustrates how a DC pulse field fully magnetizes, while a gradually diminishing AC field cycles demagnetizes (noting the latched remnant magnetization after pulsing by a pulse field of 1 msec, and demagnetization by AC current to a zero magnetic moment); FIG. 17(*b*) illustrates a TEM of a Fe—Cr—Co stainless steel magnet spinodally decomposed into two-phase microstructure; FIG. 17(*c*) illustrates a TEM of the Fe—Cr—Co stainless steel magnet of FIG. 17(*b*) after deformation elongated to induce shape-anisotropy.

Figure 18:
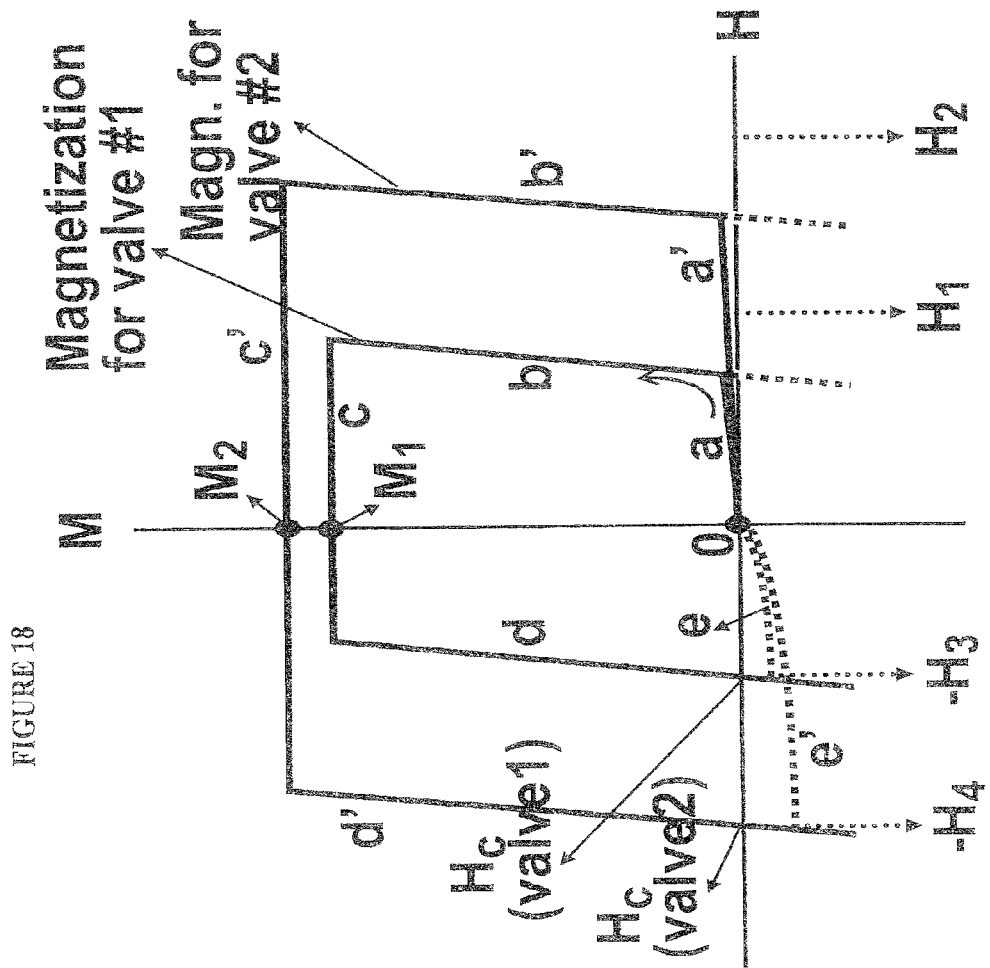
FIG. 18 graphically illustrates the exemplary embodiment comprising use of remote magnetic field manipulation of nano-depot valve openings and closings, as discussed in detail, below.

FIG. 18 graphically illustrates the exemplary embodiment comprising use of remote magnetic field manipulation of nano-depot valve openings and closings. One aspect of this invention provides devices for therapeutics and/or diagnostics, and delivering multiple compounds, e.g., drugs, tracers, biologics and the like, which need to be delivered simultaneously or sequentially. The magnetization and demagnetization curves in FIG. 18 illustrate how the two types of valves (e.g., valve #1 and valve #2 in FIG. 18), e.g., as illustrated in FIG. 16, can have a different coercive force (e.g., by switching field values; this can done by using materials combinations or processing variations) and can be manipulated to close or open independently; for example, alternative embodiments comprise:

In one embodiment, due to the slight self-demagnetization because of the base magnet and the cantilever magnet having finite dimensions, the M-H magnetization loop is slightly skewed as in FIG. 18 for easier control of magnetization-demagnetization operations.

In one embodiment, with an applied field of $H_2$ and field removal to zero, both valves #1 and #2 are magnetized to $M_1$ and $M_2$ near-saturation and are closed by magnetic attraction.

In one embodiment, after AC demagnetization with gradually diminishing field cycles, e.g., 60 Hz for a fraction of or a few seconds from greater than (>) $H_2$ to H=0, both valves are demagnetized and open.

In one embodiment, if a field $H_1$ is applied and removed after demagnetization, only valve #1 is magnetized to $M_1$ and closed (valve #2 remains open).

In one embodiment, if the field is then increased to $H_2$ and removed, valve #2 is also magnetized to $M_2$ and closed, so both valves are made closed sequentially. Up to 3-4 valves can sequentially or separately manipulated by different switching field materials of the valve.

In one embodiment, if both valves are magnetized/closed first (at $M_1$ and $M_2$ state), and then a DC demag cycle of abcde is applied (to field —$H_3$ then H=0), only valve #1 is demagnetized and open (valve #2 remains closed). If a cycle of a' b' c' d' e' is applied (to field —$H_4$ then H=0), the valve #2 is also made open. Up to 3-4 valves can sequentially be open.

In one embodiment, one of the main advantages of this compound-delivery (e.g., tracer-, drug-delivery) device is the "latchability", which enables selective, concurrent or sequential release of several compounds (e.g., tracers, drugs) as well as a complete stop of release, with just a pulse magnetic field. There is no need to have continuous magnetic field, electrical current, or any other power requirements, thus making the device simple, more reliable and inexpensive.

Re-Entrant Nano-Depot Array with Remotely Triggerable, Temperature-Sensitive Polymers The invention provides for fabrication of a new type of nano-depot array comprising a bio-compatible or bio degradable polymer base which also contains magnetic nanoparticles for remote triggering. In one aspect, the re-entrant geometry (with a bottleneck at the entrance to the drug-stored cavity) simultaneously allows a capillary constriction near the entrance to prevent (or reduce) compound (e.g., tracer, drug) release (unless activated), together with a large volume storage capability for compounds (e.g., tracers, drugs) in the non-bottlenecked larger region. An exemplary embodiment is schematically illustrated in FIG. 19.

Figure 19:
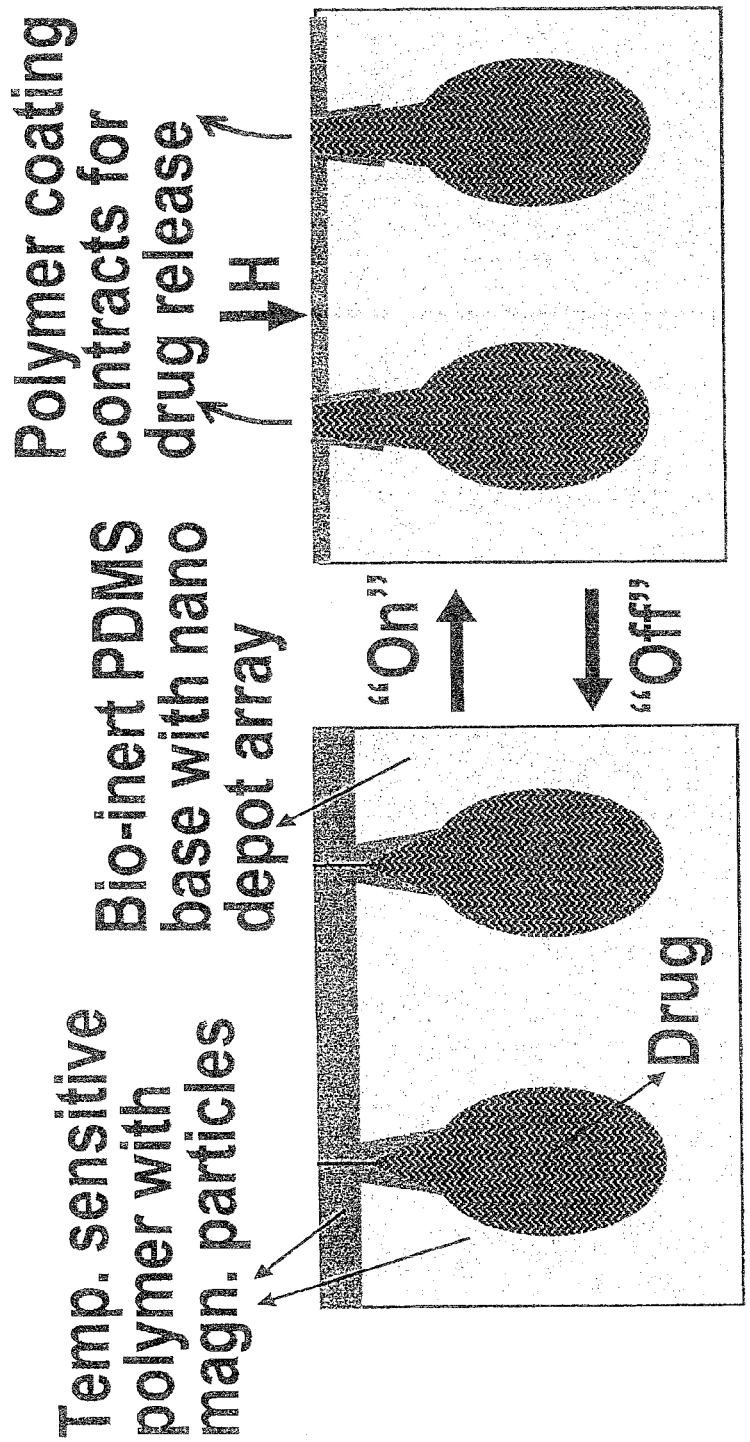
FIG. 19 schematically illustrates an exemplary re-entrant nano-depot polymer array of the invention with remotely controlled, temperature responsive, compound (e.g., tracer, drug) release, as discussed in detail, below.

FIG. 19 schematically illustrates an exemplary re-entrant nano-depot polymer array of the invention with remotely controlled, temperature responsive, compound (e.g., tracer, drug) release. In one aspect, the magnetic particles embedded in a temperature-sensitive polymer are heated or cooled for valve opening and closing by remote magnetic field.

Figure 20:
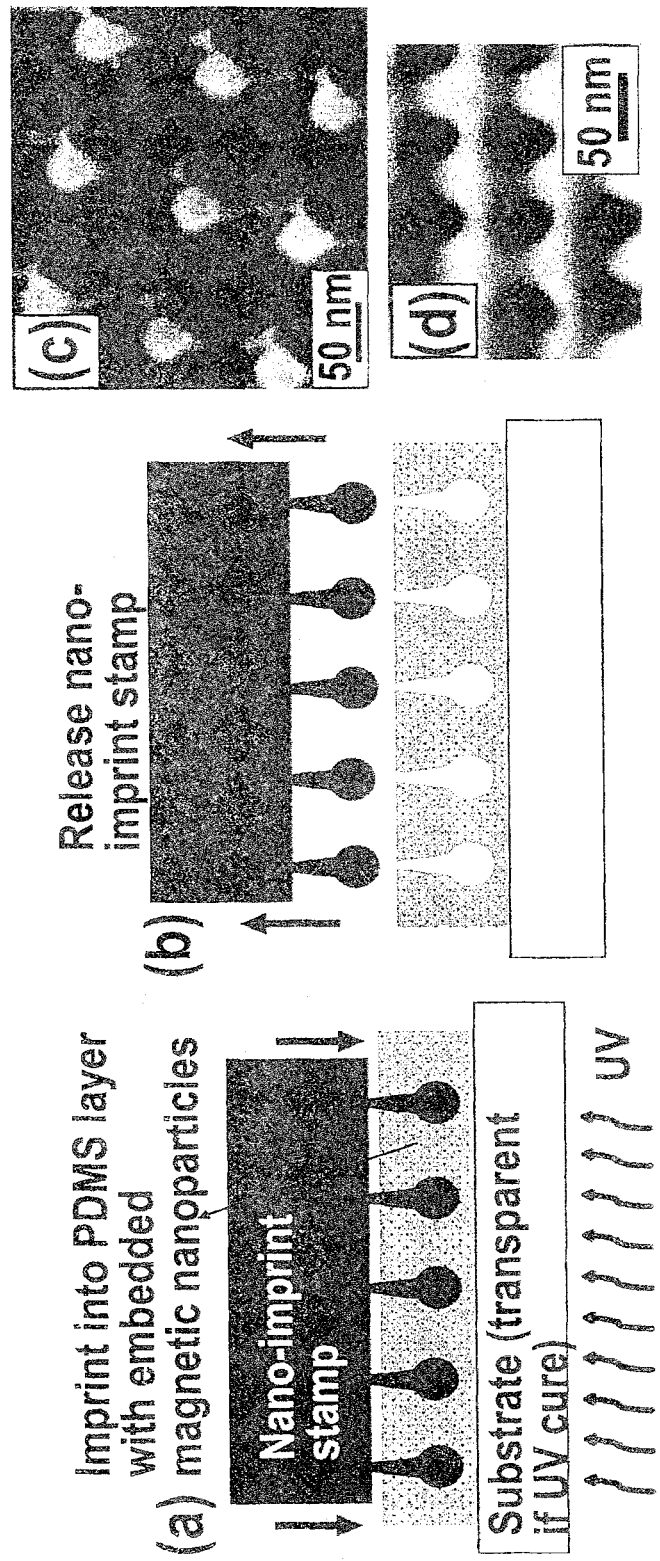
FIG. 20 illustrates an exemplary fabrication (product of manufacture) of the invention comprising an elastomeric nano-depot array made by nano-imprint lithography.

In one aspect, the re-entrant nano-depot array can be fabricated using low-cost, nano-imprint technology with pin-head-shaped imprint stamp configuration as illustrated in FIG. 20(*a*) and FIG. 20(*b*). An exemplary nano-stamp has the dimensions of about 10 to 50 nm diameter, e.g., as a nanoscale Si pin-head configuration; the nanoscale Si pin-head has been successfully fabricated by using advanced e-beam lithography, e.g., as illustrated in FIG. 20(*c*).

In one aspect, the nano-stamp is impressed into uncured elastomer such as the well known, biocompatible, poly(dimethylsiloxane) (PDMS), which can then be either catalyst-cured, temperature-cured (at ~RT to ~150° C.), or UV-cured (as illustrated in FIG. 20(*a*)) using available elastomer materials, then the nano-stamp is released by pulling upward (as illustrated in FIG. 20(*b*)) by virtue of the compliant and stretchable nature of the elastomer.

In one embodiment, this re-entrant (bottlenecked) nano-depot'ed elastomer is then partially covered with a thin layer of temperature sensitive polymer (as illustrated in FIG. 19, left drawing) by spin coating or dip coating. This thermally shrinkable polymer layer is pre-mixed with temperature-responsive magnetic nanoparticles such as an approximately 10 to 50 nm diameter $Fe_3O_4$ nanoparticles during the synthesis of the polymer coating material.

In one embodiment, poly(NIPPAm) or a modified copolymer such as (IPPAAm-co-DMAAm-co-BMA) with adjusted composition is used to increase the swelling transition temperature (lower critical solution temperature (LCST)) to somewhat above the human body temperature for external triggering of temperature-responsive compound (e.g., tracer, drug) release (as described e.g., in reference 28, below) is used as the coating layer.

In one aspect, for compound (e.g., tracer, drug) release "on" mode, an external magnetic RF field (e.g., 100 KHz) is applied to heat the magnetic nanoparticles (see e.g., FIG. 4), which shrinks the coated temperature-sensitive copolymer to slightly above the body temperature for opening of the nano-depot containing the drugs. For drug release "off" mode, one simply needs to turn off the magnetic field, which cools down the copolymer to expand and close the nano-depot entrance.

In summary, FIG. 20 illustrates an exemplary fabrication (product of manufacture) of the invention comprising an elastomeric nano-depot array made by nano-imprint lithography: FIG. 20(a) illustrates an exemplary press nano-imprint stamp pressed into an exemplary spin-coated PDMS (containing magnetic particles), which is illustrated as being cured by UV light and/or heating; FIG. 20(b) illustrates release (withdrawal) of the stamp; FIG. 20(c) illustrates a TEM of an exemplary nano-imprint stamp of the invention comprising a protruding, pin-head type pillar array; and FIG. 20(d) illustrates a TEM of an exemplary PDMS nano-imprinted pattern with an equi-diameter pillar array nano-stamp.

In one aspect, for operation of the on-off switchable compound (e.g., tracer, drug) delivery, e.g., including the delivery of proteins, hormones, nucleic acids or living cells, various materials parameters are optimized, for example, the sphere size, shell thickness, nanoporosity of the shell, the size of the trapped magnetic particles for various exemplary embodiments of the invention; and/or the dimensions and magnetic characteristics of materials involved for various exemplary embodiments of the invention. In one aspect, various exemplary embodiments of the invention are optimized for compound (e.g., tracer, drug) or cell delivery performance, magnetic field intensity, duration, duty cycles of on-off operations; all of these parameters can be modified depending on specific applications.

Exemplary drug systems that can be utilized for controlled on-off release include a diabetes drug insulin, a hormonal protein, dexamethasone, an anti-inflammatory and immunosuppressant steroid hormone that is used in a variety of clinical applications including both therapeutic and diagnostic uses, paclitaxel (TAXOL™), a mitotic inhibitor drug used in cancer chemotherapy, a cancer therapy compound, 1,3-bis(2-chloroethyl)-1-nitrosourea (BCNU), otherwise known as carmustine used in brain tumor therapy, and the like. In alternative embodiments, any one of these compounds can be radio-labeled and the release amount can be quantified (as described e.g., in reference 11, listed below) using a scintillation counter. In alternative embodiments, to determine in vivo drug release efficacy, any standard procedure of taking blood or urine samples and measuring drug or drug metabolite levels, for example, using an HPLC, can be employed.

References

1. Controlled Drug Delivery: Challenges and Strategies, edited by Kinam Park, American Chemical Society, Washington D.C., 1997.

2. Biorelated Polymers and Gels, edit. Teruo Okano, Academic Press, New York, 1998.

3. Enhancement in Drug Delivery, edit. Elka Touitou and Brian Barry, CRC Press, 2006.

4. Nanoparticulate Drug Delivery Systems, edited by D. Thassu, M. Deleers, and Y. Pathak, Information Healthcare, Inc., 2007.

5. Y. Kaneko and T. Okano, Temperature responsive hydrogels as intelligent materials, Chap. 2, Biorelated Polymers and Gels, edited by Teruo Okano, Academic Press, New York, 1998.

6. K. Sawahata, M. Hara, H. Yasunaga, and Y. Osada, J. Contr. Rel. 14, 253-262 (1990).

7. Joseph Kost, Jackie Wolfrum, and Robert Langer, Magnetically enhanced in diabetic rats, J. Biomed. Mater. Res. 21, 1367-1373 (1987).

8. T. Shimoboji, E. Larenas, T. Fowler, S. Kulkarni, A. S. Hoffman, and P. S. Stayton, Photoresponsive polymer-enzyme switches, PNAS 99(26), 16592-16596 (2002).

9. S. M. Henry, M. E. H. El-Sayed, C. M. Pirie, P. S. Stayton, and A. S. Hoffman, "pH-Responsive Poly(styrene-alt-maleic anhydride) Copolymers for Intracellular Drug Delivery", Biomacromol. 7, 2407-14 (2006).

10. John T. Santini, Jr, Michael J. Cima and Robert Langer, "A controlled-release microchip", Nature 397, 335-338 (1999).

11. Y. Li, R. S. Shawgo, B. Tyler, P. T. Henderson, J. S. Vogel, A. Rosenberg, P. B. Storm, R. Langer, H. Brem, M. J. Cima, In vivo release from a drug delivery MEMS device, J. Contr. Rel. 100, 211-219 (2004).

12. Y. Yin, R. M. Rioux, C. K. Erdonmez, S. Hughes, G. A. Somorjai, A. Paul Alivisatos, "Formation of Hollow Nanocrystals Through the Nanoscale Kirkendall Effect", Science 304, 711-714 (2004).

13. Yugang Sun, Brian T. Mayers, and Younan Xia, "Template-Engaged Replacement Reaction: A One-Step Approach to the Large-Scale Synthesis of Metal Nanostructures with Hollow Interiors", Nano Lett. 2(5), 481-485 (2002).

14. S. W. Kim, M. Kim, W. Y. Lee, and T. Hyeon, "Fabrication of Hollow Palladium Spheres and Their Successful Application to the Recyclable Heterogeneous Catalyst for Suzuki Coupling Reactions", J. Am. Chem. Soc. 124, 7642-7643 (2002).

15. J. Y. Lee and S. H. Hong, J. H. Lee, Y. K. Lee and J. Y. Choi, "Uniform Coating of Nanometer-Scale BaTiO3 Layer on Spherical Ni Particles via Hydro-thermal Conversion of Ti-Hydroxide", J. Am. Ceram. Soc., 88(2), 303-307 (2005).

16. H. P. Liang, L. J. Wan, C. L. Bai, and L. Jiang, "Gold Hollow Nanospheres: Tunable Surface Plasmon Resonance Controlled by Interior-Cavity Sizes", J. Phys. Chem. B109, 7795-7800 (2005).

17. A. Jordan, R. Scholz, K. Maier-Hauff, M. Johannsen, P. Wust, J. Nadobny, H. Schirra, H. Schmidt, S. Deger, S. Loening, W. Lanksch and R. Felix, "Presentation of a new magnetic field therapy system for the treatment of human solid tumors with magnetic fluid hyperthermia", J. Magn. Magn. Mater. 225, 118-126 (2001).

18. V. S. Kalambur, B. Han, B. E. Hammer, T. W. Shield and J. C. Bischof, "In vitro characterization of movement, heating and visualization of magnetic nanoparticles for biomedical applications", Nanotechnology 16, 1221-1233 (2005).

19. F. Scherer, M. Anton, U. Schillinger, J. Henke, C. Bergemann, A. Krüger, B. Gansbacher and C. Plank, "Magnetofection: enhancing and targeting gene delivery by magnetic force in vitro and in vivo", Nature/Gene Therapy 9(2), 102-109 (2002).

20: Q. A. Pankhurst, J. Connolly, S. K. Jones and J. Dobson, "Applications of magnetic nanoparticles in biomedicine", J. Phys. D: Appl. Phys. 36, R167-R181 (2003).

21. C. Loo, L. Hirsch, M. H. Lee, E. Chang, J. West, N. Halas, and R. Drezek "Gold nanoshell bioconjugates for molecular imaging in living cells", Optics Lett. 30, 1012-1014 (2005).

22. C. Loo, A. Lowery, N. Halas, J. West, and R. Drezek, "Immunotargeted Nanoshells for Integrated Cancer Imaging and Therapy", Nano Lett. 5(4), 709-711 (2005).

23. J. Chen, F. Saeki, B. J. Wiley, H. Cang, M. J. Cobb, Z. Y. Li, L. Au, H. Zhang, M. B. Kimmey, X. Li, and Y. Xia, "Gold Nanocages: Bioconjugation and Their Potential Use as Optical Imaging Contrast Agents", Nano Lett. 5(3), 473-477 (2005).

24. S. Jin and G. Y. Chin, "Fe—Cr—Co Magnets (Invited)", IEEE Trans. Magn. MAG-23, 3187-3192 (1987).

25. S. Jin and N. V. Gayle, "Low Cobalt Cr—Co—Fe Magnet Alloys by Slow Cooling Under Magnetic Field", IEEE Trans. Magnetics, MAG-16, 526-528 (1980).

26. S. Jin, R. B. van Dover, R. C. Sherwood and T. H. Tiefel, "Magnetic Sensors Using Fe—Cr—Ni Alloys with Square Hysteresis Loops", J. Appl. Phys. 55, 2620-2622 (1984).

27. S. Jin, H. Mavoori, R. P. Espindola, and T. A. Strasser, "Broad-Range Latchable Reconfiguration of Bragg Wavelength in Optical Gratings", Appl. Phys. Lett. 74, 2259-2261 (1999).

28. R. Yoshida, K. Sakai, T. Okano, and Y. Sakurai, "Modulating the Phase Transition Temperature and Thermosensitivity in N-isopropylacrilamide Copolymer Gels", J. Biomater. Sci., Polymer Ed. 6, 585-588 (1994).

29. L. A. Guzman, V. Labhasetwar, C. Song, Y. Jang, A. M. Lincoff, R. Levy, E. J. Topol, "Local Intraluminal Infusion of Biodegradable Polymeric Nanoparticles: A Novel Approach for Prolonged Drug Delivery after Balloon Angioplasty", Circulation 94(6), 1441-1448 (1996).

A number of embodiments of the invention have been described. Nevertheless, it will be understood that various modifications may be made without departing from the spirit and scope of the invention. Accordingly, other embodiments are within the scope of the following claims.

What is claimed is:

1. A nanosphere or nanodevice, comprising:
    (a) a layer, body or coating comprising an elastomeric material,
    wherein the layer, body or coating comprises a plurality of internal reservoirs or hollow depots each having a communication to the exterior; and
    (b) an outer polymer layer partially or completely covering the elastomeric material comprising a temperature-sensitive polymer, a temperature-responsive bio-compatible polymer or a bio-degradable temperature-responsive polymer comprising:
        (i) a plurality of magnetic, heat-responsive or ultrasonic-responsive particles or nanoparticles embedded therein, and
        (ii) a plurality of actuatable pores or nanopores communicating with the plurality of internal reservoirs or hollow depots in the elastomeric material,
    wherein the outer polymer layer shrinks upon heating, resulting in partial or complete opening of the actuatable pores or nanopores, and cooling of the outer polymer layer partially or completely expands and closes or constricts the actuatable pores or nanopores,
    without destroying the integrity of the nanosphere or nanodevice.

2. The nanosphere or nanodevice of claim 1, wherein the average diameter of a magnetic, heat-responsive or ultrasonic-responsive particle or nanoparticle embedded in the outer polymer layer is the is between about 10 to 100 nm.

3. The nanosphere or nanodevice of claim 1, wherein the temperature-sensitive polymer, temperature-responsive biocompatible polymer or bio-degradable temperature-responsive polymer comprises a material selected from the group consisting of: a poly(NIPPAm), an IPPAAm-co-DMAAm-co-BMA, a poly lactic acid (PLA) polymer, a glycollic acid polymer, a polylactic-polyglycolic acid (PLGA) copolymer, a dextran, a dextran grafted with a poly (N-isopropylacrylamide-co-N,N-dimethylacrylamide), an elastomeric poly (phosphoester urethane), a polycaprolactone (PCL) polymer, a polyhydroxybutyrate (PHB) polymer, a PEG modified PLGA, a surface modified PLGA with poly(L-lysine)-g-poly (ethylene glycol) (PLLg-PEG), a polystyrene, a polymethyl methacrylate (PMMA), and any combination thereof.

4. The nanosphere or nanodevice of claim 1, wherein the outer polymer layer is formed by a chemical precipitation, a sol-gel synthesis, an emulsion process, a displacement reaction, an electroless deposition, an electrochemical deposition, or a chemical or a physical vapor deposition inside a fluidized bed.

5. The nanosphere or nanodevice of claim 1, wherein the temperature-sensitive polymer, temperature-responsive biocompatible polymer or bio-degradable temperature-responsive polymer comprises a material selected from the group consisting of: a poly(dimethylsiloxane) (PDMS), a poly(NIPPAm), an IPPAAm-co-DMAAm-co-BMA, and a mixture thereof.

6. The nanosphere or nanodevice of claim 1, wherein the magnetic, heat-responsive or ultrasonic-responsive particles or nanoparticles embedded in the outer layer comprise:
    (1) a material selected from the group consisting of: an oxide of Fe, Ni, Co, an alloy thereof and any combination thereof, or
    (2) a material selected from the group consisting of: an Au; a Pt; a Pd; a stainless steel; an alloy thereof and any combination thereof;
    (3) a material selected from the group consisting of: a Ni; a Cu; a Co; an Fe or an Fe oxide particle and any combination thereof;
    (4) a material selected from the group consisting of: an $Fe_2O_3$, an $Fe_3O_4$; a ceramic; a silicon oxide; an aluminum oxide; a titanium oxide; a carbon; a carbide; a graphite; a Ti-carbide; a Zr-carbide; a Si-carbide; and a mixture thereof.

7. The nanosphere or nanodevice of claim 6, wherein the $Fe_3O_4$ particles or nanoparticles have an average diameter of between about 10 to 50 nm.

8. The nanosphere or nanodevice of claim 1, wherein the embedded magnetic, heat-responsive or ultrasonic-responsive particles or nanoparticles comprise a material selected from the group consisting of: a gold (Au), a platinum (Pt), a palladium (Pd), a silica, a silicon dioxide ($SiO_2$) or a polymer thereof, a graphite, a Ni, a Cu, a Co, an Fe particle, a Ni oxide, a Cu oxide, a Co oxide, a Fe oxide, and a mixture thereof.

9. The nanosphere or nanodevice of claim 1, wherein the plurality of internal reservoirs or hollow depots comprise a material selected from the group consisting of: a drug, a tracer, a biological agent and a mixture thereof.

10. The nanosphere or nanodevice of claim 1, wherein the outer polymer layer is pre-mixed with the plurality of magnetic, heat-responsive or ultrasonic-responsive particles or nanoparticles embedded therein during the synthesis of the outer polymer layer.

11. The nanosphere or nanodevice of claim 1, wherein an outer surface of the outer polymer layer comprises a targeting molecule.

12. The nanosphere or nanodevice of claim 11, wherein the targeting molecule comprises a material selected from the group consisting of: an antibody, a ligand to a receptor or a cytokine receptor, an antibody that specifically binds a target cell or a cancer cell, and any combination thereof.

13. The nanosphere or nanodevice of claim 1, wherein the average diameter of a magnetic, heat-responsive or ultrasonic-responsive particle or nanoparticle embedded in the outer polymer layer is between about 20 to 80 nm.

14. The nanosphere or nanodevice of claim 1, further comprising a partially oxidized outer surface to protect against oxidation.

15. The nanosphere or nanodevice of claim 1, further comprising an inert metal coated outer surface.

16. The nanosphere or nanodevice of claim 1, wherein the plurality of internal reservoirs or hollow depots comprise a material selected from the group consisting of: an insulin, a hormonal protein, dexamethasone, an anti-inflammatory, an immunosuppressant, a steroid hormone, a paclitaxel, a mitotic inhibitor drug, a cancer therapy compound, a 1,3-bis (2-chloroethyl)-1-nitrosourea (BCNU), and any combination thereof.

17. The nanosphere or nanodevice of claim 1, wherein the plurality of internal reservoirs or hollow depots comprise a material selected from the group consisting of: a radio-label, a radioactive isotope, a polysaccharide, a nucleic acid, a vector or a plasmid, and any combination thereof.

18. The nanosphere or nanodevice of claim 1, wherein the elastomeric material comprises a material selected from the group consisting of: a poly (phosphoester urethane), a polycaprolactone (PCL) polymer, a polyhydroxybutyrate (PHB) polymer, a PEG modified PLGA, a surface modified PLGA with poly(L-lysine)-g-poly(ethylene glycol) (PLLg-PEG), a polystyrene, a polymethyl methacrylate (PMMA) and a mixture thereof.

19. The nanosphere or nanodevice of claim 1, wherein the plurality of actuatable pores or nanopores communicating with the plurality of internal reservoirs or hollow depots in the elastomeric material have a pore diameter of about 15 nm.

20. The nanosphere or nanodevice of claim 19, wherein the plurality of actuatable pores or nanopores communicating with the plurality of internal reservoirs or hollow depots in the elastomeric material have a pore diameter of about 6 nm.

21. The nanosphere or nanodevice of claim 20, wherein the plurality of actuatable pores or nanopores communicating with the plurality of internal reservoirs or hollow depots in the elastomeric material have a pore diameter of about 2 nm.

* * * * *